United States Patent
Yuan et al.

(10) Patent No.: US 10,759,905 B2
(45) Date of Patent: Sep. 1, 2020

(54) BIODEGRADABLE AMPHIPHILIC POLYMER, POLYMERIC VESICLES PREPARED THEREFROM, AND APPLICATION OF BIODEGRADABLE AMPHIPHILIC POLYMER IN PREPARATION OF MEDICINES FOR TARGETED THERAPY OF LUNG CANCER

(71) Applicant: BrightGene Bio-Medical Technology Co., Ltd., Suzhou, Jiangsu (CN)

(72) Inventors: Jiandong Yuan, Suzhou (CN); Fenghua Meng, Jiangsu (CN); Yan Zou, Jiangsu (CN); Yuan Fang, Jiangsu (CN); Zhiyuan Zhong, Jiangsu (CN)

(73) Assignee: BrightGene Bio-Medical Technology Co., Ltd., Suzhou, Jiangsu Province (CN)

( * ) Notice: Subject to any disclaimer, the term of this patent is extended or adjusted under 35 U.S.C. 154(b) by 144 days.

(21) Appl. No.: 16/064,317

(22) PCT Filed: Dec. 21, 2016

(86) PCT No.: PCT/CN2016/111385
§ 371 (c)(1),
(2) Date: Jun. 20, 2018

(87) PCT Pub. No.: WO2017/107934
PCT Pub. Date: Jun. 29, 2017

(65) Prior Publication Data
US 2020/0062897 A1 Feb. 27, 2020

(30) Foreign Application Priority Data
Dec. 22, 2015 (CN) .......................... 2015 1 0973770

(51) Int. Cl.
| | |
|---|---|
| C08G 64/18 | (2006.01) |
| C08G 64/30 | (2006.01) |
| A61K 49/18 | (2006.01) |
| A61K 47/62 | (2017.01) |
| A61K 47/68 | (2017.01) |
| A61K 9/127 | (2006.01) |
| A61K 47/34 | (2017.01) |
| C08G 64/02 | (2006.01) |
| C08G 64/08 | (2006.01) |
| B82Y 5/00 | (2011.01) |

(52) U.S. Cl.
CPC .......... *C08G 64/183* (2013.01); *A61K 9/1273* (2013.01); *A61K 47/34* (2013.01); *A61K 47/62* (2017.08); *A61K 47/6835* (2017.08); *C08G 64/0241* (2013.01); *C08G 64/081* (2013.01); *C08G 64/305* (2013.01); *B82Y 5/00* (2013.01); *C08G 2230/00* (2013.01)

(58) Field of Classification Search
None
See application file for complete search history.

(56) References Cited

U.S. PATENT DOCUMENTS

| | | | |
|---|---|---|---|
| 10,072,122 B2 * | 9/2018 | Meng | C08G 64/30 |
| 2017/0019083 A1 | 1/2017 | Fukae et al. | |
| 2018/0044315 A1 * | 2/2018 | Zhong | A61K 47/34 |

FOREIGN PATENT DOCUMENTS

| | | | | |
|---|---|---|---|---|
| CN | 102657873 A | 9/2012 | | |
| CN | 103930412 A | 7/2014 | | |
| CN | 104031248 A | 9/2014 | | |
| CN | 104610538 | * 5/2015 | ............. | C08G 64/18 |
| CN | 104610538 A | 5/2015 | | |

OTHER PUBLICATIONS

International Search Report dated Mar. 30, 2017 in PCT application No. PCT/CN2016/111385.

* cited by examiner

*Primary Examiner* — Brian Gulledge
(74) *Attorney, Agent, or Firm* — Fish & Richardson P.C.

(57) ABSTRACT

Disclosed in the present disclosure is a biodegradable amphiphilic polymer containing disulfide in the side chain, a self-crosslinked polymeric vesicle thereof and an application in the targeted therapy of lung cancer. The polymer is obtained by an activity-controllable ring-opening polymerization based on a cyclic carbonate monomer containing a functional group of dithiolane ring, which has a controllable molecular weight and a narrow molecular weight distribution, and does not require processes of protection and deprotection; the polymer obtained by the ring-opening polymerization of the cyclic carbonate monomer of the present disclosure has biodegradability and can be used to control the drug release system, the prepared lung cancer-targeted reduction-sensitive reversibly-crosslinked polymeric vesicle as a nanomedicine carrier supports stable long circulation in vivo. However, it is highly enriched in lung cancer tissues, enter cells efficiently, and rapidly decrosslinks in the cells to release drugs, so as to kill cancer cells with high potency and specificity and inhibit the growth of tumor effectively without causing toxic and side effects.

9 Claims, 5 Drawing Sheets

BIODEGRADABLE AMPHIPHILIC POLYMER, POLYMERIC VESICLES PREPARED THEREFROM, AND APPLICATION OF BIODEGRADABLE AMPHIPHILIC POLYMER IN PREPARATION OF MEDICINES FOR TARGETED THERAPY OF LUNG CANCER

TECHNICAL FIELD

The present disclosure relates to a biodegradable polymer material and an application thereof, in particular, to a biodegradable amphiphilic polymer containing functional groups of dithiolane rings as side groups, a polymeric vesicle, and an application in targeted therapy of lung cancer. The present disclosure belongs to the field of medical materials.

BACKGROUND

Biodegradable polymers have very unique properties and thus being widely used in various fields of biomedicine, such as surgical sutures, bone fixation devices, scaffold materials for biological tissue engineering, carriers for controlled-release drugs, and the like. Synthetic biodegradable polymers mainly include aliphatic polyesters (polyglycolide PGA, polylactide PLA, lactide-glycolide copolymer PLGA, polycaprolactone PCL), polycarbonate (polytrimethylene cyclic carbonate PTMC), etc., which are the most commonly used biodegradable polymers, and have been approved by the US Food and Drug Administration (FDA).

However, the existing biodegradable polymers, such as PTMC, PCL, PLA and PLGA, have relatively simple structures, lack of modifiable functional groups, and are usually hard to provide a drug carrier stable in circulation or a stable surface modified coating. The degradation products of polycarbonates are mainly carbon dioxide and neutral glycols, with no acidic degradation products generated. Among these, a functional cyclic carbonate monomer can be copolymerized with cyclic ester monomers such as GA, LA and ε-CL, and other cyclic carbonate monomers, to obtain biodegradable polymers with different properties.

In addition, the biodegradable nanocarriers obtained from the biodegradable polymers prepared by the prior art have the problems of instability in in vivo circulation, low uptake of tumor cells, and low intracellular concentration of drug, which result in the low potency of nanomedicines along with toxic and side effects. Micellar nanoparticles can be prepared from the functional biodegradable polymer, which are stable in in vivo circulation. However, the micellar nanoparticles can only be loaded with hydrophobic small molecule anticancer drugs, but is inability for hydrophilic small molecule anticancer drugs with strong penetrating property and for hydrophilic bio-macromolecular drugs having low toxic and side effects such as protein drugs and nucleic acid drugs, thus greatly limiting their application as drug carriers.

Cancer is the main killer threatening human health. The morbidity and mortality of cancer have been increasing year by year. The incidence of lung cancer in the world, especially in China, remains high. Surgery can only be beneficial to patients in early stage of lung cancer but ineffective to patients in middle and late stages. The treatment of lung cancer is featured by difficulties in early diagnosis, poor prognosis, easy metastasis and easiness in developing drug resistance. Nanomedicine is a key point and hope for the treatment of lung cancer. However, in the prior art, there is still a lack of high-potency nanomedicines which are stable in in vivo circulation, specifically target lung cancer, release drug rapidly within cells, and have low toxic and side effects. In particular, there is a lack of nanocarriers capable of transporting hydrophilic small molecule anticancer drugs.

SUMMARY

An object of the present disclosure is to provide a biodegradable amphiphilic polymer, polymeric vesicles prepared therefrom, and an application thereof as a carrier for anti-lung cancer drugs in the preparation of lung cancer-targeting therapeutic drugs.

In order to achieve the above-mentioned object, the specific technical solutions of the present disclosure are given below.

A biodegradable amphiphilic polymer, of which the chemical structure is:

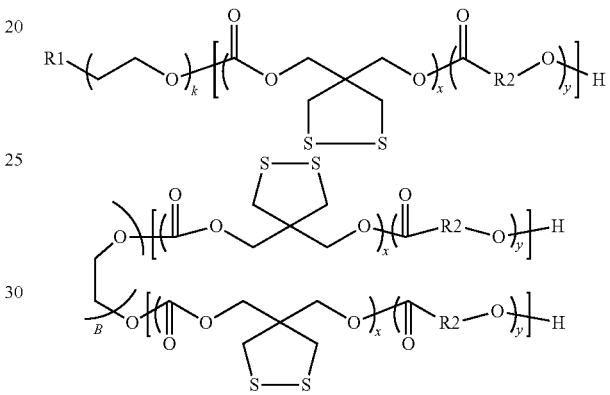

wherein R1 is selected from one of the following groups:

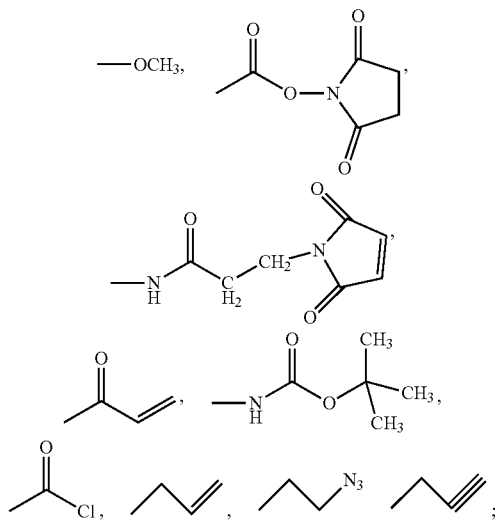

R2 is selected from one of the following groups:

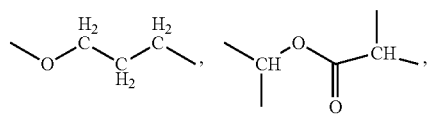

-continued

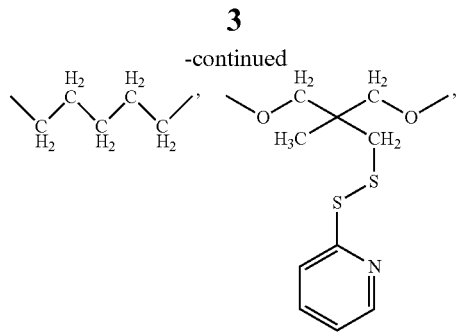

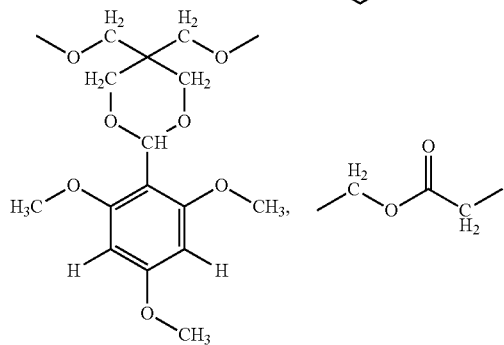

wherein k ranges from 43 to 170, x ranges from 10 to 30, y ranges from 40 to 200, m ranges from 86 to 340.

The biodegradable amphiphilic polymer disclosed in present disclosure, comprising a hydrophobic block that contains a cyclic carbonate unit containing a functional group of dithiolane ring, can be a diblock polymer:

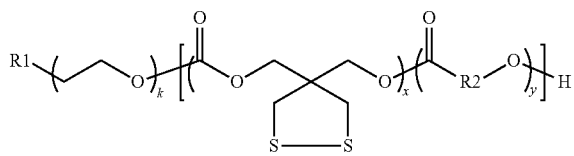

or a triblock polymer:

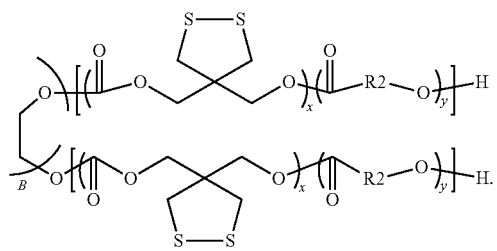

In a preferred technical solution, R1 is selected from one of the following groups:

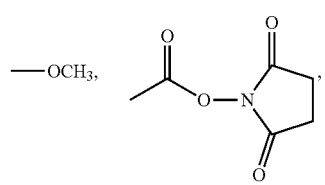

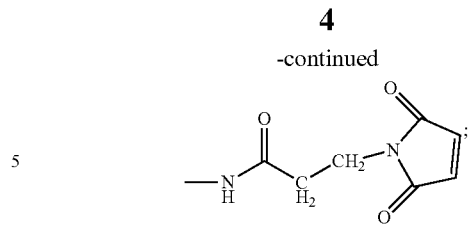

R2 is selected from one of the following groups:

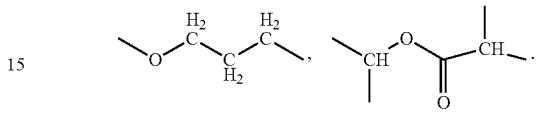

Preferably, in the chemical structures of the above-mentioned biodegradable amphiphilic polymer, k ranges from 113 to 170, x ranges from 20 to 26, y ranges from 100 to 190, m ranges from 226 to 340.

The above-mentioned biodegradable amphiphilic polymer contains disulfide in the side chain, which can be obtained in a solvent from the ring-opening polymerization of a cyclic carbonate monomer containing a functional group of dithiolane ring with other cyclic ester monomers and cyclic carbonate monomers in the presence of an initiator; said other cyclic carbonate monomers include trimethylene cyclic carbonate (TMC), cyclic carbonate containing trimethoxybenzylidene in its side chain (PTMB-PEC), cyclic carbonate containing dithiopyridine in its side chain (PDSC), and acrylate trimethylolethane cyclic carbonate (AEC). Said other cyclic ester monomers include lactide (LA), glycolide (GA) and caprolactone (CL).

The cyclic carbonate monomer containing a functional group of dithiolane ring (CDC) has the following chemical structure:

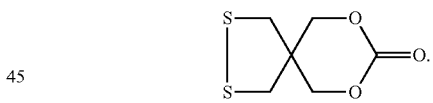

For example, the above-mentioned cyclic carbonate monomer (CDC) can be ring-opening copolymerized with TMC in methylene chloride, with monomethoxypolyethylene glycol as an initiator and zinc bis[bis(trimethylsilyl) amide] as a catalyst, to form a diblock polymer with CDC units and TMC units randomly arranged; the reaction formula thereof is as follows:

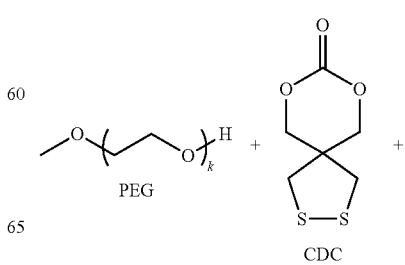

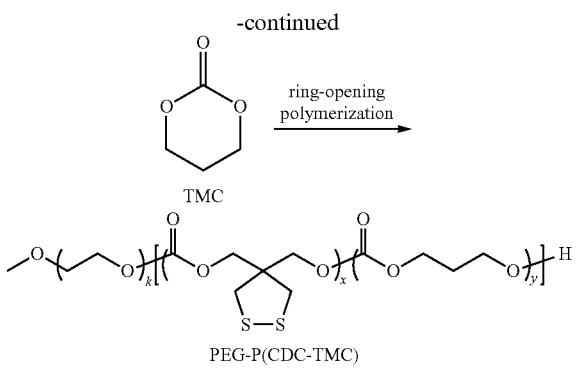

TMC

PEG-P(CDC-TMC)

The disclosed amphiphilic polymer containing disulfide in the side chain has biodegradability, the molecular weight of the hydrophobic portion thereof is three times or more that of the hydrophilic portion. It can be used to prepare the structure of the polymeric vesicles by methods such as solvent displacement method, dialysis method, or thin-film hydration method. The prepared polymeric vesicle (polymersome) is nano-sized and has a particle size of 40-180 nm, which can be used as a carrier for drugs for lung cancer treatment. A hydrophobic small molecule anti-lung cancer drug such as paclitaxel and docetaxel is loaded in the hydrophobic membrane of the polymeric vesicle; or a hydrophilic anti-lung cancer drug, in particular a hydrophilic small molecule anticancer drug, such as doxorubicin hydrochloride, epirubicin hydrochloride, irinotecan hydrochloride, and mitoxantrone hydrochloride, can also be loaded in large hydrophilic inner cavities of the polymeric vesicle. In this way, it overcomes the defect that the existing micellar carriers formed of amphiphilic polymers can only be loaded with hydrophobic drugs and the defect that there is no carrier in the prior art which can be efficiently loaded with the hydrophilic small molecule anticancer drugs and be stable in in vivo circulation. The terminus of the hydrophilic portion PEG of the above-mentioned biodegradable amphiphilic polymer can be chemically coupled to a tumor-specific targeting molecule such as peptides like cRGD, cNGQ, or cc-9, etc., to prepare a tumor-specific targeted biodegradable amphiphilic polymer.

The present disclosure also discloses a polymeric vesicle, which can be prepared from the above-mentioned biodegradable amphiphilic polymer, or prepared from the above-mentioned tumor-specific targeted biodegradable amphiphilic polymer, or prepared from the above-mentioned biodegradable amphiphilic polymer and the tumor-specific targeted biodegradable amphiphilic polymer. For example, the above-mentioned biodegradable amphiphilic polymer and the tumor-specific targeted biodegradable amphiphilic polymer can be mixed in different proportions to prepare polymeric vesicles with different density of targeting ligands, i.e., to obtain the lung cancer-targeted self-crosslinked polymeric vesicles, so as to increase the intake of polymersomal nanomedicines in lung cancer cells. Or, the outer surface of the cross-linked polymeric vesicles or the self-crosslinked polymeric vesicles prepared from the biodegradable amphiphilic polymer can also be coupled to tumor cell-specific targeting molecules to prepare the lung cancer-targeted cross-linked polymeric vesicles and the lung cancer-targeted self-crosslinked polymeric vesicles, thus increasing the intake of lung cancer cells. For example, cRGD, cNGQ, or cc-9 are bonded at the PEG terminus of the polymeric vesicles via Michael addition.

The above-mentioned biodegradable amphiphilic polymer and the tumor-specific targeted biodegradable amphiphilic polymer can be self-crosslinked without adding any substance, thereby obtaining the self-crosslinked polymeric vesicles and the lung cancer-targeted self-crosslinked polymeric vesicles; or, under the catalysis of a reducing agent such as dithiothreitol (DTT) or glutathione (GSH) in catalytic amount, can be used to prepare the cross-linked polymeric vesicles and the lung cancer-targeted cross-linked polymeric vesicles. The self-crosslinked polymeric vesicles, the lung cancer-targeted self-crosslinked polymeric vesicles, the cross-linked polymeric vesicles and the lung cancer-targeted cross-linked polymeric vesicles form stable chemical crosslinks within the hydrophobic membrane of the polymeric vesicles, so as to allow stable long circulation in vivo. However, after endocytosis into the cancer cells, in the presence of a great amount of reducing substances within cells, the formed crosslinks are rapidly released (decrosslinked), the drug is rapidly released to kill lung cancer cells efficiently. Therefore, the present disclosure claims the application of the above-mentioned biodegradable amphiphilic polymer in the preparation of nanomedicines for the treatment of lung cancer; further, the present disclosure also discloses the application of the above-mentioned polymeric vesicles in the preparation of nanomedicines for the treatment of lung cancer, including the application of the polymeric vesicles and the self-crosslinked polymeric vesicles prepared by the biodegradable amphiphilic polymer containing disulfide in the side chain, and the lung cancer-targeted self-crosslinked polymeric vesicles and the lung cancer-targeted crosslinked polymeric vesicles prepared by the tumor-specific targeted biodegradable amphiphilic polymer alone or together with the biodegradable amphiphilic polymer in the preparation of nanomedicines for targeted therapy of lung cancer. The anti-lung cancer nanomedicines prepared based on the polymer of the present disclosure are anti-lung cancer polymersomal nanomedicines.

Attributed to the implementation of the above-mentioned solution, the present disclosure has the following advantages as compared to the prior art.

1. The present disclosure utilizes a cyclic carbonate monomer containing a functional group of dithiolane ring, with polyethylene glycol as an initiator, through the activity-controllable ring-opening polymerization to copolymerize with TMC or LA to obtain the biodegradable amphiphilic polymer containing disulfide in the side chain with a controllable molecular weight and a narrow molecular weight distribution; as the dithiolane ring group does not affect the ring-opening polymerization of the cyclic carbonate monomer, the polymerization process does not require the processes of protection and deprotection in the prior art, which simplifies the operation steps.

2. The disclosed biodegradable amphiphilic polymer containing disulfide in the side chain has biodegradability, can be used to prepare the polymeric vesicles and the lung cancer-targeted polymeric vesicles and loaded with drugs of different nature, and can be self-crosslinked without adding any substance to form stable self-crosslinked polymersomal nanomedicines, so as to overcome the defects of the nanomedicines in the prior art, i.e., instability in in vivo circulation, easy and early drug release, and toxic and side effects.

3. The crosslinking of the disclosed self-crosslinked polymersomal nanomedicines has reversibility, that is, the disclosed self-crosslinked polymersomal nanomedicines support long circulation in vivo and can be highly enriched in lung cancer cells; however, it rapidly decrosslinks after entering lung cancer cells to release drug, thus achieving efficient and specific killing of lung cancer cells without toxic and side effects. In this way, the present disclosure overcomes the defects of the cross-linked nanomedicines in the prior art, i.e., being over stable and thereby leading to slow drug release in cells and causing drug resistance.

4. The disclosed biodegradable polymeric vesicles and lung cancer-targeted polymeric vesicles can be used to prepare the self-crosslinked polymeric vesicles without adding any substance, allowing a simple preparation method, thereby overcoming the defects existed in the preparation of the crosslinked nanomedicines in the prior art, i.e., crosslinking agent and other substances must be added, complex operation and purification process are required, and so on.

5. The self-crosslinked polymeric vesicles prepared by the self-assembly of the disclosed amphiphilic polymer can be used in a controlled release system of hydrophilic small molecule anticancer drugs, thereby overcoming the defect that the existing biodegradable nano-micellar carriers are only applicable for loading hydrophobic small molecule drugs and the defect that there is no carrier in the prior art which can be efficiently loaded with the hydrophilic small molecule anticancer drugs and be stable in in vivo circulation. Further, the self-crosslinked polymeric vesicles can be used to prepare the lung cancer-targeted self-crosslinked polymeric vesicles, which have wider application value in the aspect of high-efficient targeted therapy of lung cancer.

DETAILED DESCRIPTION

The present disclosure is further described with reference to the Examples and the attached drawings.

Example 1 Synthesis of the Cyclic Carbonate Monomer Containing a Functional Group of Dithiolane Ring (CDC)

Sodium hydrosulfide monohydrate (28.25 g, 381.7 mmol) was dissolved in 400 mL of N, N-dimethylformamide (DMF) and heated to complete dissolution at 50° C. Dibromoneopentyl glycol (20 g, 76.4 mmol) was added dropwise and reacted for 48 hours. The reactant was distilled under a reduced pressure to remove the solvent DMF, then diluted with 200 mL of distilled water, extracted four times with 250 mL of ethyl acetate, and finally the organic phase was evaporated by rotary evaporation to give a yellow viscous Compound A, yield: 70%; Compound A dissolved in 400 mL of tetrahydrofuran (THF) was left in air for 24 hours so that the intermolecular mercapto group was oxidized to sulfur-sulfur bond to give Compound B, yield: >98%; Compound B (11.7 g, 70.5 mmol) was dissolved in the dried THF (150 mL) under nitrogen protection and stirred until complete dissolution. The solution was then cooled to 0° C., ethyl chloroformate (15.65 mL, 119.8 mmol) was added therein, then $Et_3N$ (22.83 mL, 120.0 mmol) was added dropwise. After the addition was completed, the system continued to react in an ice-water bath for 4 hours. After the reaction was completed, the produced $Et_3N.HCl$ was filtered off, the filtrate was concentrated by rotary evaporation, and finally recrystallized with ether for many times to give a yellow crystal, i.e., the cyclic carbonate monomer containing a functional group of dithiolane ring (CDC), yield: 64%.

Figure 1:
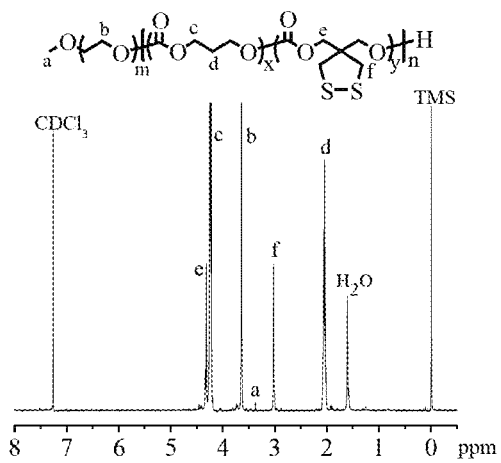
FIG. 1 shows the H-NMR spectrum of the polymer PEG5k-P(CDC4.9k-co-TMC19k) prepared by the method of Example 2.

Example 2 Synthesis of the Diblock Polymer PEG5k-P(CDC4.9k-co-TMC19k) Containing Dithiolane Rings as Side Groups Under a nitrogen atmosphere, 0.1 g (0.52 mmol) of CDC monomer and 0.4 g (3.85 mmol) of trimethylene carbonate (TMC) were dissolved in 3 mL of methylene chloride, and added to a sealed reactor, then 0.1 g (0.02 mmol) of CH$_3$O-PEG5000 and 0.5 mL of zinc bis[bis(trimethylsilyl) amide] in methylene chloride (0.1 mol/L) as catalyst were added. Then, the reactor was sealed and transferred out of the glove box. After 2 days of reaction at 40° C. in an oil bath, the reaction was stopped by glacial acetic acid and precipitated in ice-cold ether, and finally filtered and dried in vacuum to obtain PEGSk-P(CDC4.9k-co-TMC19.0k). The NMR spectrum was shown in FIG. 1, $^1$H NMR (400 MHz, CDCl$_3$): 2.08 (t, —COCH$_2$CH$_2$CH$_2$O—), 3.08 (s, —CCH$_2$), 3.30 (m, —OCH$_3$), 3.65 (t, —OCH$_2$CH$_2$O—), 4.28 (t, —COCH$_2$CH$_2$CH$_2$O—), 4.31 (m, —CCH$_2$). In the following formula, k=114, x=26 and y=186 were calculated by NMR. Molecular weight measured by GPC: 34.5 kDa, molecular weight distribution: 1.48.

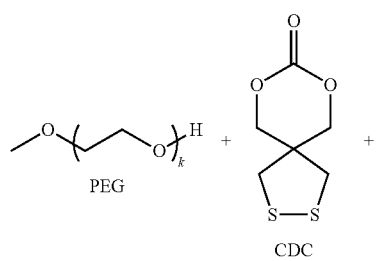

PEG

CDC

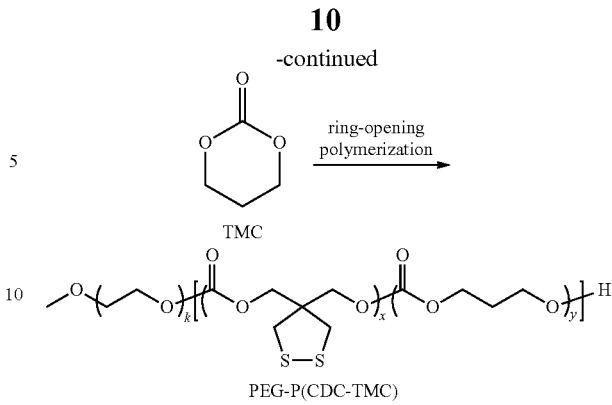

TMC

PEG-P(CDC-TMC)

Example 3 Synthesis of Diblock Polymer Mal-PEG6k-P(CDC4.8k-Co-TMC19.2k) Containing Dithiolane Rings as Side Groups Under a nitrogen atmosphere, 0.1 g (0.52 mmol) of CDC monomer and 0.4 g (3.85 mmol) of TMC were dissolved in 3 mL of methylene chloride and added to a sealed reactor; then 0.12 g (0.02 mmol) of Mal-PEG6000 and 0.1 mol/L of zinc bis[bis(trimethylsilyl)amide] in methylene chloride (0.1 mol/L) as catalyst were added; then the reactor was sealed and transferred out of the glove box. After reacting in an oil bath at 40° C. for 2 days, the reaction was stopped by glacial acetic acid and precipitated in ice-cold ether, and finally filtered and dried in vacuum to give Mal-PEG6k-P (CDC4.8k-co-TMC19.2k). $^1$H NMR (400 MHz, CDCl$_3$): 2.08 (t, —COCH$_2$CH$_2$CH$_2$O—), 3.08 (s, —CCH$_2$), 3.30 (m, —OCH$_3$), 3.65 (t, —OCH$_2$CH$_2$O—), 4.28 (t, —COCH$_2$CH$_2$CH$_2$O—), 4.31 (m, —CCH$_2$), and 6.70 (s, Mal). In the following formula, k=136, x=25, and y=188 were calculated by NMR. Molecular weight measured by GPC: 38.6 kDa, molecular weight distribution: 1.42.

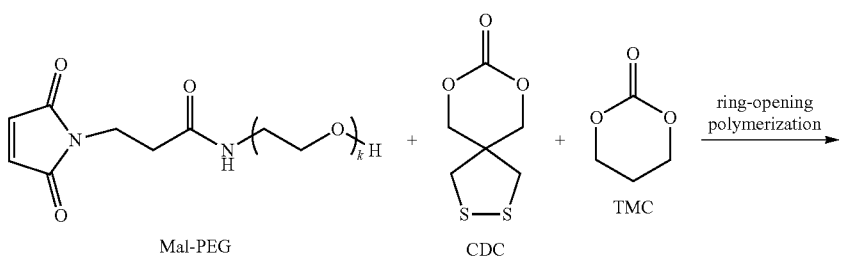

Mal-PEG    CDC    TMC

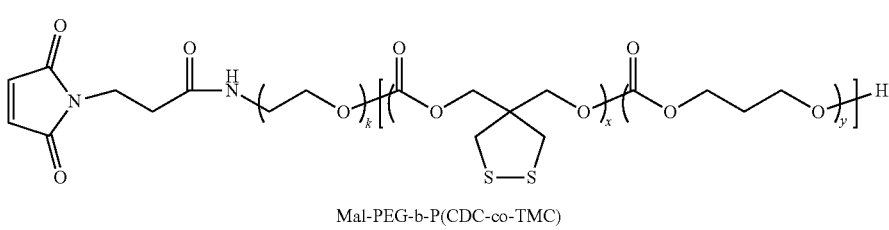

Mal-PEG-b-P(CDC-co-TMC)

Example 4 Synthesis of Diblock Polymer NHS-PEG6.5k-P(CDC4.6k-co-TMC18.6k) Containing Disulfide in the Side Chain Under a nitrogen atmosphere, 0.1 g (0.52 mmol) of CDC monomer and 0.4 g (3.85 mmol) of TMC were dissolved in 3 mL of methylene chloride and added to a sealed reactor; then 0.1 g (0.015 mmol) of NHS-PEG6500 and 0.5 mL of zinc bis[bis(trimethylsilyl)amide] in methylene chloride (0.1 mol/L) as catalyst were added thereto; then the reactor was sealed and transferred out of the glove box. After reacting in an oil bath at 40° C. for 2 days, the reaction was stopped by glacial acetic acid and precipitated in ice-cold ether, and finally filtered and dried in vacuum to give NHS-PEG6.5k-P(CDC4.6k-co-TMC18.6k). $^1$H NMR (400 MHz, CDCl$_3$): 2.08 (t, —COCH$_2$CH$_2$CH$_2$O—), 3.08 (s, —CCH$_2$), 3.30 (m, —OCH$_3$), 3.65 (t, —OCH$_2$CH$_2$O—), 4.28 (t, —COCH$_2$CH$_2$CH$_2$O—), 4.31 (m, —CCH$_2$), and 2.3 (s, NHS). In the following formula, k=145, x=24.0, and y=182 were calculated by NMR. Molecular weight measured by GPC: 37.6 kDa, molecular weight distribution: 1.38.

Figure 2:
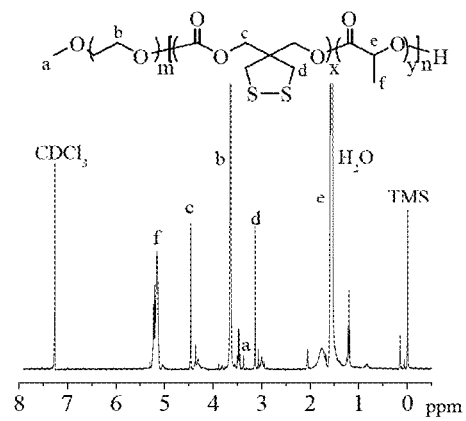
FIG. 2 shows the NMR spectrum of the polymer PEG5k-P(CDC3.7k-co-LA14.6k) prepared by the method of Example 6.

Example 6 Synthesis of Diblock Polymer PEG5k-P(CDC3.7k-co-LA14.6k) Containing Disulfide in the Side Chain Under a nitrogen atmosphere, 0.08 g (0.42 mmol) of CDC and 0.3 g (2.1 mmol) of lactide (LA) were dissolved in 2 mL of methylene chloride and added to a sealed reactor; then 0.1 g (0.02 mmol) of CH$_3$O-PEG5000 and 0.1 mol/L of zinc bis[bis(trimethylsilyl)amide] in methylene chloride (0.1 mL) as catalyst were added thereto. After reacting in an oil bath at 40° C. for 2 days, the post-treatment was the same as that in Example 2 to obtain PEGSk-P(CDC3.7k-co-LA14.6k). NMR spectrum was shown in FIG. 2, $^1$H NMR (400 MHz, CDCl$_3$): 1.59 (s, —COCH(CH$_3$)O—), 3.08 (s, —CCH$_2$), 3.30 (m, —OCH$_3$), 3.65 (t, —OCH$_2$CH$_2$O—), 4.31 (m, —CCH$_2$), 5.07 (s, —COCH(CH$_3$)O—). In the following formula, k=114, x=19, and y=101 were calculated by NMR. Molecular weight measured by GPC: 24.3 kDa, molecular weight distribution: 1.32.

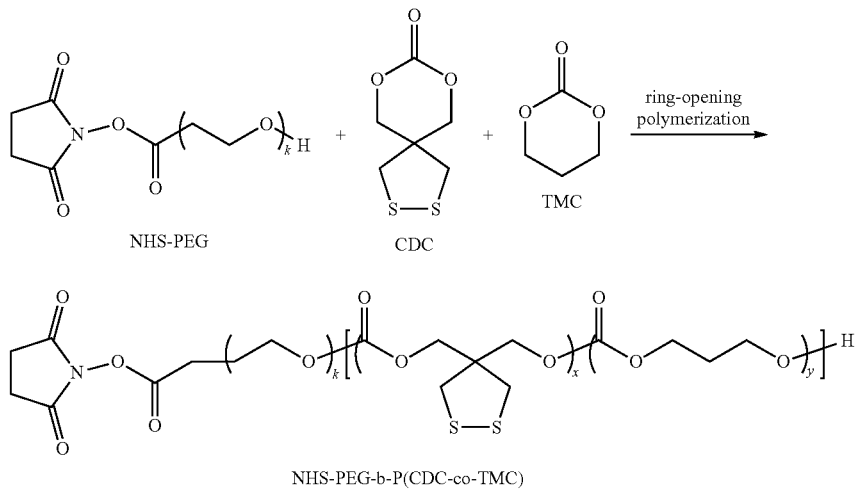

NHS-PEG-b-P(CDC-co-TMC)

Example 5 Synthesis of Diblock Polymer PEG1.9k-P(CDC1.9k-co-TMC4.1k) Containing Dithiolane Rings as Side Groups Under a nitrogen atmosphere, 0.1 g (0.52 mmol) of CDC monomer and 0.2 g (1.93 mmol) of TMC were dissolved in 1 mL of methylene chloride and added to a sealed reactor; then 0.1 g (0.05 mmol) of CH$_3$O-PEG1900 and 0.5 mL of zinc bis[bis(trimethylsilyl)amide] in methylene chloride (0.1 mol/L) as catalyst were added thereto. After reacting in an oil bath at 40° C. for 2 days, the post-treatment was the same as that in Example 2 to obtain PEG1.9k-P(CDC1.9k-co-TMC3.9k). The reaction formula and the characteristic peaks in $^1$H NMR spectrum were the same as those of Example 2. In the following formula, k=46, x=10, and y=40 were calculated by NMR. Molecular weight measured by GPC: 14.5 kDa, molecular weight distribution: 1.36.

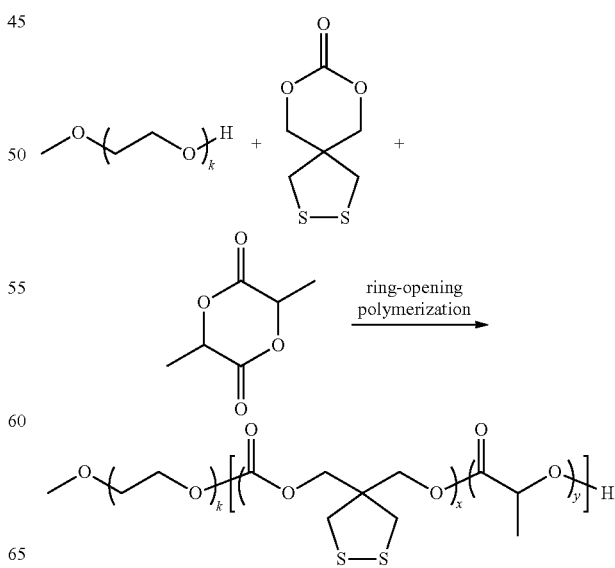

Example 7 SYNTHESIS OF DIBLOCK POLYMER PEG6.5k-P(CDC5.8k-co-LA28.3k) Containing Disulfide in the Side Chain Under a nitrogen atmosphere, 0.1 g (0.57 mmol) CDC and 0.5 g (3.5 mmol) of LA were dissolved in 3 mL of methylene chloride and added to a sealed reactor; then 0.11 g (0.015 mmol) of CH$_3$O-PEG6500 and 0.5 mL of zinc bis[bis(trimethylsilyl)amide] in methylene chloride (0.1 mol/L) as catalyst were added thereto. After reacting in an oil bath at 40° C. for 2 days, the post-treatment was the same as that in Example 2 to give PEG6.5k-P(CDC5.8k-co-LA28.3k). The reaction formula and the characteristic peaks in $^1$H NMR spectrum were the same as those of Example 6. In the following formula, k=148, x=30, y=200 were calculated by NMR. Molecular weight measured by GPC: 42.4 kDa, molecular weight distribution: 1.43

Example 8 Synthesis of Diblock Polymer Mal-PEG6k-P(CDC3.6k-co-LA18.6k) Containing Disulfide in the Side Chain Under a nitrogen atmosphere, 0.1 g (0.52 mmol) of CDC and 0.5 g (5.56 mmol) of LA were dissolved in 4 mL of methylene chloride and added to a sealed reactor; then 0.15 g (0.025 mmol) of Mal-PEG6000 and 0.1 mol/L of zinc bis[bis(trimethylsilyl)amide] in methylene chloride (0.1 mL) as catalyst were added thereto. After reacting in an oil bath at 40° C. for 2 days, the post-treatment was the same as that in Example 2 to give Mal-PEG6k-P(CDC3.6k-co-LA18.6k). $^1$H NMR (400 MHz, CDCl$_3$): 1.59 (s, —COCH(CH$_3$)O—), 3.08 (s, —CCH$_2$), 3.30 (m, —OCH$_3$), 3.65 (t, —OCH$_2$CH$_2$O—), 4.31 (m, —CCH$_2$), 5.07 (s, —COCH(CH$_3$)O—), and 6.70 (s, Mal). In the following formula, k=136, x=19, and y=129 were calculated by NMR. Molecular weight measured by GPC: 32.5 kDa, molecular weight distribution: 1.44.

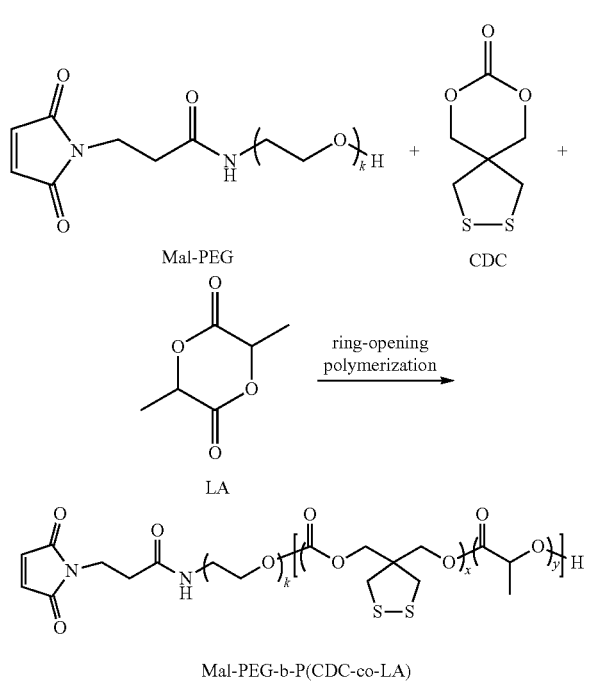

Example 9 Synthesis of Triblock Polymer P(CDC3.8k-TMC18.8k)-PEG5k-P(CDC3.8k-TMC18.8k Under a nitrogen atmosphere, 0.8 g (7.84 mmol) of TMC and 0.16 g (0.83 mmol) of CDC were dissolved in 8 mL of methylene chloride and added to a sealed reactor; then 0.1 g (0.02 mmol) of HO-PEG-OH5000 and 1 mL of zinc bis[bis(trimethylsilyl)amide] in methylene chloride (0.2 mol/L) as catalyst were added thereto. After reacting in an oil bath at 40° C. for 2 days, the post-treatment was the same as that in Example 2 to give the triblock polymer P(CDC3.8k-TMC18.8k)-PEG5k-P(CDC3.8k-TMC18.8k).
The characteristic peaks in $^1$H NMR spectrum were the same as those in Example 2. In the following formula, m=114, x=20, and y=184 were calculated by NMR. Molecular weight measured by GPC: 78.9 kDa, molecular weight distribution: 1.54.

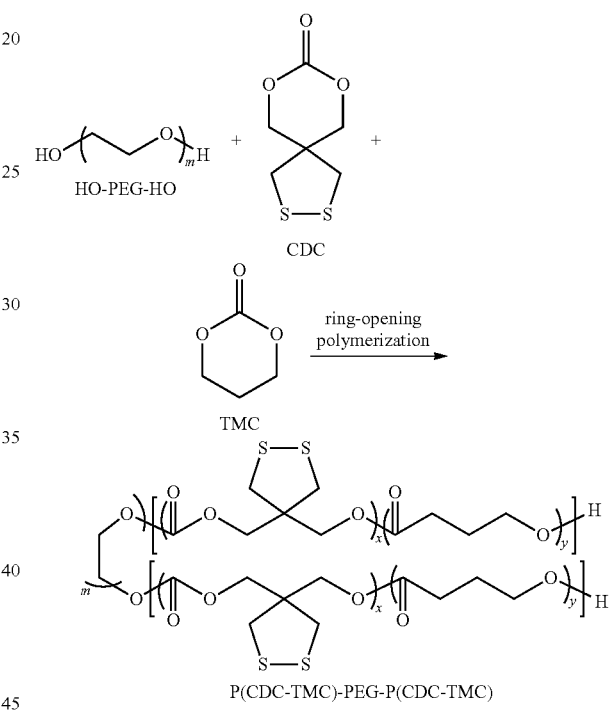

Example 10 Synthesis of Diblock Polymer NHS-PEG7.5k-P(CDC3.8k-co-LA13.8k) Containing Disulfide in the Side Chain Under a nitrogen atmosphere, 0.1 g (0.52 mmol) of CDC and 0.4 g (2.8 mmol) of LA were dissolved in 3 mL of methylene chloride and added to a sealed reactor; then 0.013 mmol of NHS-PEG7500 and 1 mL of zinc bis[bis(trimethylsilyl)amide] in methylene chloride (0.1 mol/L) as catalyst were added thereto; the reactor was sealed and transferred out of the glove box, and reacted in an oil bath at 40° C. for 2 days. The post-treatment was the same as that in Example 2 to give NHS-PEG7.5k-P(CDC4.8k-co-LA19.0k). $^1$H NMR (400 MHz, CDCl$_3$): 1.59 (s, —COCH(CH$_3$)O—), 3.08 (s, —CCH$_2$), 3.30 (m, —OCH$_3$), 3.65 (t, —OCH$_2$CH$_2$O—), 4.31 (m, —CCH$_2$), 5.07 (s, —COCH(CH$_3$)O—) and 2.3 (s, NHS). In the following formula, k=170, x=20, and y=96 were calculated by NMR. Molecular weight measured by GPC: 42.3 kDa, molecular weight distribution: 1.45.

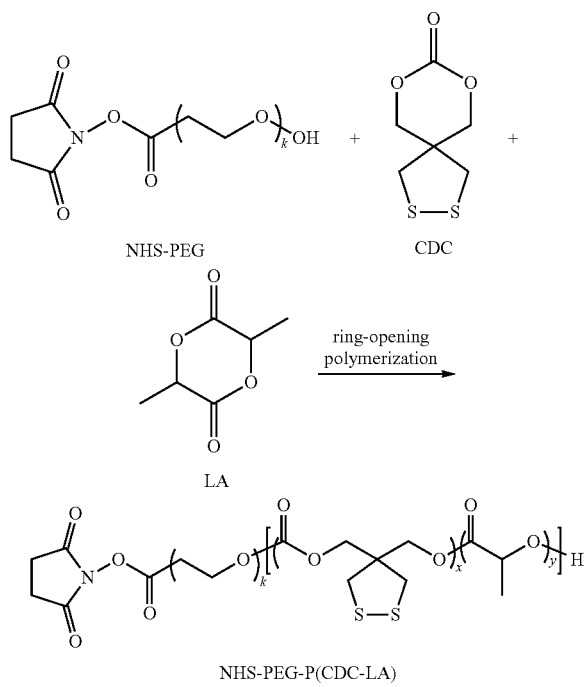

NHS-PEG-P(CDC-LA)

Example 11 Synthesis of Targeted Diblock Polymer CC9-PEG7.5k-P(CDC3.8k-co-LA13.8k The synthesis of the polymer CC9-PEG7.5k-P(CDC3.8k-co-LA13.8k) coupled with cyclic polypeptide CSNIDARAC (cc9) was divided into two steps. The first step was to prepare NHS-PEG7.5k-P(CDC3.8k-co-LA13.8k) as in Example 10; the second step was bonding CC9 thereto through amidation reaction. The above-mentioned polymer NHS-PEG7.5k-P(CDC3.8k-co-LA13.8k) was first dissolved in DMF, with twice the molar weight of CC9 added thereto. After reacting at 30° C. for two days, CC9-PEG6.5k-P(CDC3.8k-co-LA13.8k) was obtained by dialysis and freeze drying. The grafting ratio of CC9 was calculated to be 91% by the analysis of NMR and BCA protein kit.

Example 12 Synthesis of Targeted Diblock Polymer cRGD-PEG6k-P(CDC3.6k-co-LA18.6k The synthesis of the polymer cRGD-PEG6k-P(CDC3.6k-co-LA18.6k) coupled with cyclic polypeptide c(RGDfC) (cRGD-SH) was divided into two steps. The first step was to prepare Mal-PEG6k-P(CDC3.6k-co-LA18.6k) as in Example 8; the second step was bonding the mercapto group of cRGD-SH thereto by Michael addition reaction. The polymer Mal-PEG6k-P(CDC3.6k-co-LA18.6k) was first dissolved in 0.5 ml of DMF, with 2 ml of borate buffer solution (pH 8.0) followed by 1.5 times molar weight of cRGD-SH added thereto. After reacting at 30° C. for two days, the final product cRGD-PEG6k-P(CDC3.6k-co-LA18.6k) was obtained by dialysis and freeze drying. The grafting ratio of cRGD was calculated to be 94% by the analysis of NMR and BCA protein kit.

Example 13 Synthesis of Targeted Diblock Polymer cRGD-PEG6.5k-P(CDC4.6k-co-TMC18.6k The synthesis of the polymer cRGD-PEG6.5k-P(CDC4.6k-co-TMC18.6k) coupled with cyclic polypeptide c(RGDfK) (cRGD) was divided into two steps. The first step was to prepare NHS-PEG6.5k-P(CDC4.6k-co-TMC18.6k) as in Example 4; the second step was bonding the amino group of cRGD thereto through amidation reaction. The above-mentioned polymer NHS-PEG6.5k-P(CDC4.6k-co-TMC18.6k) was first dissolved in DMF, with twice the molar weight of cRGD added thereto. After reacting at 30° C. for two days, free cRGD was removed by dialysis; and cRGD-PEG6.5k-P(CDC4.6k-co-TMC18.6k) was obtained by freeze drying. The grafting ratio of cRGD was calculated to be 88% by the analysis of NMR and BCA protein kit.

Example 14 Synthesis of Targeted Diblock Polymer cNGQ-PEG6.5k-P(CDC4.6k-co-TMC18.6k The synthesis of the polymer cNGQ-PEG6.5k-P(CDC4.6k-co-TMC18.6k) coupled with cyclic polypeptide cNGQGEQc (cNGQ) was divided into two steps. The first step was to prepare NHS-PEG6.5k-P(CDC4.6k-co-TMC18.6k) as in Example 4; the second step was bonding the amino group of cNGQ thereto through amidation reaction. The above-mentioned polymer NHS-PEG6.5k-P(CDC4.6k-co-TMC18.6k) was first dissolved in DMF, with twice the molar weight of cNGQ added thereto. After reacting at 30° C. for two days, free cNGQ was removed by dialysis and cNGQ-PEG6.5k-P(CDC4.6k-co-TMC18.6k) was obtained by freeze drying. The grafting ratio of cNGQ was calculated to be 92% by the analysis of NMR and BCA protein kit.

A variety of biodegradable amphiphilic polymers containing disulfide in the side chain could be prepared by preparation methods similar to the above-mentioned methods. The proportion of raw materials and the characterization thereof were shown in Table 1.

TABLE 1

Preparation Conditions for Each Polymer, NMR Results and GPC Characterization Results of the Products

| Polymer | Feed capacity for preparation (mmol) | | | Number of repeat units (NMR) | | | Molecular weight (kg/mol) | | PDI |
|---|---|---|---|---|---|---|---|---|---|
| | PEG | CDC | TMC, LA, PDSC, CL, GA | k or m | x | y | NMR | GPC | GPC |
| PEG5k-P(CDC4.9k-TMC19k) | 0.02 | 0.52 | 3.85 | 114 | 26 | 186 | 28.9 | 34.5 | 1.48 |
| Mal-PEG6k-P(CDC4.9k-TMC19k) | 0.017 | 0.52 | 3.85 | 136 | 25 | 188 | 29.9 | 38.6 | 1.42 |

TABLE 1-continued

Preparation Conditions for Each Polymer, NMR Results and GPC Characterization Results of the Products

| Polymer | Feed capacity for preparation (mmol) | | | Number of repeat units (NMR) | | | Molecular weight (kg/mol) | | PDI |
|---|---|---|---|---|---|---|---|---|---|
| | PEG | CDC | TMC, LA, PDSC, CL, GA | k or m | x | y | NMR | GPC | GPC |
| NHS-PEG6.5k-P(CDC4.6k-TMC18.6k) | 0.015 | 0.52 | 3.85 | 145 | 24 | 182 | 29.7 | 37.6 | 1.38 |
| PEG1.9k-P(CDC1.9k-TMC4.0k) | 0.05 | 0.52 | 2.06 | 43 | 10 | 40 | 7.8 | 14.5 | 1.36 |
| PEG6.5k-P(CDC5.8k-LA28.3k) | 0.015 | 0.57 | 3.47 | 148 | 30 | 200 | 36.6 | 42.4 | 1.43 |
| PEG5k-P(CDC3.7k-LA13.6k) | 0.02 | 0.42 | 2.08 | 114 | 19 | 101 | 23.3 | 24.3 | 1.32 |
| Mal-PEG6k-P(CDC3.6k-LA18.6k) | 0.025 | 0.52 | 5.56 | 136 | 19 | 129 | 28.6 | 32.5 | 1.44 |
| P(CDC3.8k-TMC18.8k)-PEG5k-P(CDC3.8k-TMC18.8k) | 0.02 | 0.83 | 7.84 | 114 | 20 | 184 | 50.2 | 78.9 | 1.54 |
| P(CDC3.8k-LA18.8k)-PEG4k-P(CDC3.8k-LA18.8k) | 0.025 | 0.52 | 2.08 | 91 | 20 | 102 | 19.4 | 31.6 | 1.43 |
| NHS-PEG7.5k-P(CDC3.8k-LA13.8k) | 0.013 | 0.52 | 2.80 | 170 | 20 | 96 | 24.1 | 42.3 | 1.45 |
| P(CDC3.8k-TMC18.8k)-PEG5k-P(CDC3.8k-TMC18.8k) | 0.02 | 0.83 | 7.84 | 114 | 20 | 184 | 60.2 | 78.9 | 1.54 |
| PEG3.4k-P(CDC1.9k-TMC4.1k) | 0.05 | 0.52 | 2.06 | 77 | 10 | 40 | 8.4 | 13.8 | 1.34 |
| PEG5k-P(CDC2.9k-TMC19k) | 0.02 | 0.31 | 3.92 | 114 | 15 | 186 | 26.9 | 32.7 | 1.49 |
| PEG5k-P(CDC3.8k-TMC19.3k) | 0.02 | 0.42 | 3.92 | 114 | 20 | 189 | 28.1 | 34.6 | 1.43 |
| PEG5k-P(CDC5.8k-TMC18.7k) | 0.02 | 0.52 | 3.92 | 114 | 30 | 183 | 29.5 | 36.8 | 1.51 |
| PEG5k-P(CDC5.7k-LA13.6k) | 0.02 | 0.52 | 2.08 | 114 | 30 | 94 | 24.4 | 30.9 | 1.42 |
| PEG5k-P(CDC1.9k-LA14.2k) | 0.02 | 0.21 | 2.08 | 114 | 10 | 99 | 21.1 | 29.7 | 1.45 |
| AA-PEG3k-P(CDC3.9k-PDSC4.8k) | 0.1 | 2.08 | 1.85 | 68 | 20 | 18 | 11.7 | 15.2 | 1.28 |
| $N_3$-PEG1.9k-P(CDC2.7k-PDSC2.6k) | 0.1 | 1.56 | 1.11 | 43 | 14 | 10 | 7.2 | 10.8 | 1.43 |
| Ally-PEG6k-P(CDC2.9k-CL14.2k) | 0.05 | 0.78 | 6.58 | 136 | 15 | 125 | 23.1 | 30.3 | 1.38 |
| AK-PEG5k-P(CDC3.8k-GA7.6k) | 0.05 | 1.04 | 3.45 | 114 | 20 | 66 | 16.4 | 21.6 | 1.48 |

Figure 3:
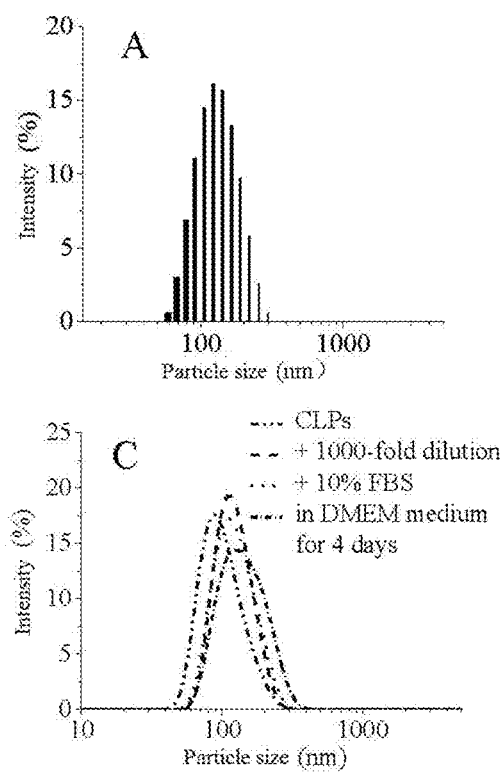
FIG. 3 shows the particle size distribution diagram (A), a transmission electron micrograph (B), a diagram of the stability test of the cross-linked polymeric vesicles (C) and a diagram of the reduction responsiveness test (D) of the cross-linked polymeric vesicle PEG5k-P(CDC4.9k-co-TMC19k) prepared by the method of Example 15.
Figure 3:
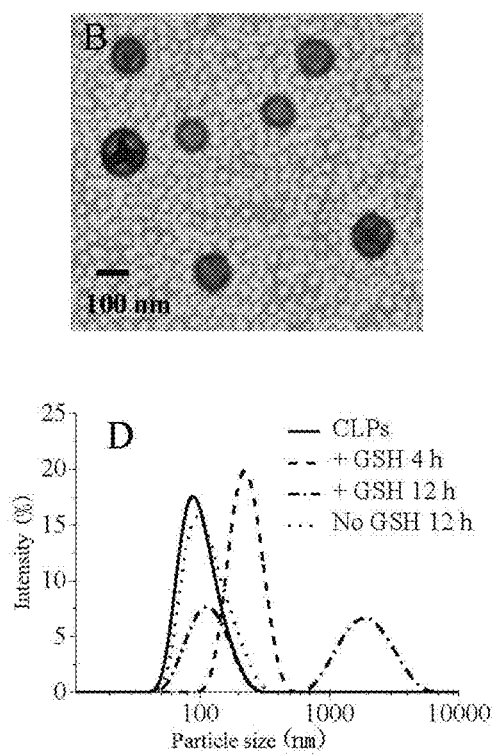

Example 15 Preparation of the Self-Crosslinked Polymeric Vesicle PEG5k-P(CDC4.9k-co-TMC19k) by Solvent Displacement Method The polymeric vesicles were prepared by solvent displacement method. 100 μL of PEG5k-P(CDC4.9k-co-TMC19k) in DMF (10 mg/mL) was added dropwise to 900 μL of phosphate buffer solution (PB, 10 mM, pH 7.4); the solution was placed in a shaker at 37° C. (200 rmp) overnight for self-crosslinking and then charged into a dialysis bag (MWCO 7000) for overnight dialysis with water being renewed for five times, the dialyzing medium was PB (10 mM, pH 7.4). The size of the resulting self-crosslinked polymeric vesicles was measured by a dynamic light scattering particle size analyzer (DLS), and the size of the formed nanovesicles was 130 nm with a narrow particle size distribution, as shown in FIG. 3A. From FIG. 3B, according to the measurement by TEM, the nanoparticles had a hollow vesicle structure. The self-crosslinked polymeric vesicles still remained unchanged particle size and particle size distribution upon high dilution or in the presence of fetal bovine serum (FIG. 3C), but were rapidly released and decrosslinked in a simulated reducing environment of tumor cells (FIG. 3D). As could be seen, the resulting polymeric vesicles could be self-crosslinked and had the reduction-sensitive decrosslinking property.

Example 16 Preparation of the Self-Crosslinked Polymeric Vesicle PEG5k-P(CDC4.9k-co-TMC19k) by Dialysis Method The polymeric vesicles were prepared by dialysis method. 100 μL of PEG5k-P(CDC4.9k-co-TMC19k) in DMF (10 mg/mL) was charged into a dialysis bag (MWCO 7000) and placed in PB (10 mM, pH 7.4) in a shaker at 37° C. (200 rmp) overnight for self-crosslinking, and then dialyzed for 24 hours in PB, with fluid being renewed for five times. According to the measurement by DLS, the cross-linked polymeric vesicles had a size of about 80 nm and a particle size distribution of 0.08.

Example 17 Preparation of the Self-Crosslinked Polymeric Vesicle PEG5k-P(CDC4.9k-co-TMC19k) by Thin-Film Hydration Method The polymeric vesicles were prepared by thin-film hydration method. 2 mg of PEG5k-P(CDC4.9k-co-TMC19k) was dissolved in 0.5 mL of a low-boiling organic solvent, such as methylene chloride or acetonitrile, to form a thin film in the bottom of a 25-mL flask with pointed bottom by rotary evaporation. Suction was continued for 24 hours under a vacuum degree of 0.1 mBar. 2 mL of PB (10 mM, pH 7.4) was added thereto. The thin film was peeled from the surface by stirring at 37° C., grinded, and then subjected to sonication for 20 min (200 rpm) and continued to stir for 24 hours. The resulting polymeric vesicles were self-crosslinked. According to the measurement by DLS, the self-crosslinked polymeric vesicles had a size of about 180 nm and a particle size distribution of 0.25.

Example 18 Preparation of the Crosslinked Polymeric Vesicle PEG5k-P(CDC4.9k-co-TMC19k) by Solvent Displacement Method The polymeric vesicles were prepared as in Example 15. After completing the dropwise addition, DTT (with a concentration of 0.09 μM) was added thereto; cross-linking was carried out at 37° C. for 12 hours and then the solution was charged into a dialysis bag (MWCO 7000) to be dialyzed overnight, with fluid being renewed for five times. The resulting self-crosslinked polymeric vesicles had a size of about 109 nm and a particle size distribution of 0.13.

Example 19 Preparation of the Targeted Self-Crosslinked Polymeric Vesicle cNGQ/PEG5k-P(CDC4.9k-co-TMC19k) Coupled with cNGQ The targeted polymer cNGQ-PEG6.5k-P(CDC4.6k-co-TMC18.6k) obtained in Example 14 and PEG5k-P(CDC4.9k-co-TMC19k) obtained in Example 2 were mixed and dissolved in DMF to prepare the targeted self-crosslinked polymeric vesicles coupled with cNGQ as in Example 15. PEG of the targeted polymer had a molecular weight larger than that of non-targeted polymer, ensuring that the targeting molecule protruded out of the surface better. When being mixed at different ratios, the two polymers could be used to prepare the self-crosslinked polymeric vesicles with different targeting molecules on the surface. A preferred embodiment was that the former had a content of 5-30 wt. %. According to the measurement by DLS, the polymeric vesicles had a size of about 90-120 nm and a particle size distribution of 0.05-0.15.

Example 20 Preparation of the Targeted Self-Crosslinked Polymeric Vesicle cRGD/PEG6.5k-P(CDC4.6k-co-TMC18.6k) Coupled with cRGD The targeted self-crosslinked polymeric vesicle coupled with cRGD was prepared by thin-film hydration method. 1.6 mg of PEG5k-P(CDC4.9k-co-TMC19k) obtained in Example 2 in DMF (10 mg/mL) and 0.4 mg of cRGD-PEG6.5k-P(CDC4.6k-co-TMC18.6k) obtained in Example 13 were dissolved in 0.5 mL of a low-boiling organic solvent such as methylene chloride or acetonitrile, the self-crosslinked polymeric vesicles as prepared in Example 17 had a size of about 88 nm and a particle size distribution of 0.08. When being mixed at different ratios, the two polymers could be used to prepare the self-crosslinked polymeric vesicles with different targeting molecules on the surface. A preferred embodiment was that the content of the former was 5-30 wt. %.

Example 21 Preparation of the Targeted Self-Crosslinked Polymeric Vesicle CC9/P(CDC3.8k-LA18.8k)-PEG4k-P(CDC3.8k-LA18.8k) Coupled with CC9

Mal-PEG6k-P(CDC3.6k-LA18.6k) prepared in Example 8 and P(CDC3.8k-LA18.8k)-PEG4k-P(CDC3.8k-LA18.8k) were mixed to prepare polymeric vesicles according to the dialysis method of Example 16. Then, 0.5 ml of 4M borate buffer solution (pH 8.0) was added to adjust the pH of the solution to 7.5-8.0. CC9 was then added at 1.5 times the molar weight of Mal, and was bonded by Michael addition reaction. After reacting for 2 days at 30° C., dialysis was carried out. According to the measurement by DLS, the polymeric vesicles had a size of 110 nm and a particle size distribution of 0.16. The grafting ratio of the polypeptide was calculated to be 90% by the analysis of NMR and BCA protein kit. When being mixed at different ratios, the two polymers could be used to prepare the self-crosslinked polymeric vesicles with different targeting molecules on the surface. A preferred embodiment was that the content of the former was 5-30 wt. %.

A variety of self-crosslinked polymeric vesicles and targeted self-crosslinked polymeric vesicles could be prepared by preparation methods similar to the above methods. The proportion of raw materials and the characterization thereof were shown in Table 2.

TABLE 2

Preparation and Characterization of the Self-Crosslinked Polymeric vesicles and the Targeted Self-Crosslinked Polymeric vesicles

| Polymer | Solvent displacement method | Dialysis method | Thin-film hydration method | Size (nm) | Particle size distribution |
|---|---|---|---|---|---|
| PEG5k-P(CDC3.7k-co-LA14.6k) | √ | | | 130 | 0.14 |
| PEG5k-P(CDC4.9k-co-TMC19k) | √ | | | 102 | 0.11 |
| cRGD20/PEG5k-P(CDC4.9k-co-TMC19k) | | | √ | 88 | 0.08 |
| cNGQ20/PEG5k-P(CDC4.9k-co-TMC19k) | | √ | | 96 | 0.18 |
| PEG2k-P(CDC1.9k-TMC4.1k) | | | √ | 67 | 0.12 |
| PEG6.5k4(CDC5.8k-LA28.3k) | √ | | | 178 | 0.20 |
| PEG3.4k-P(CDC1.9k-TMC4.1k) | | √ | | 42 | 0.15 |
| P(CDC3.8k-TMC18.8k)-PEG5k-P(CDC3.8k-TMC18.8k) | | | √ | 143 | 0.21 |
| N$_3$-PEG1.9k-P(CDC2.7k-PDSC2.6k) | | √ | | 100 | 0.13 |
| AA-PEG3k-P(CDC3.9k-PDSC4.8k) | √ | | | 162 | 0.18 |
| Ally-PEG6k-P(CDC2.9k-CL14.2k) | | | √ | 124 | 0.21 |
| AK-PEG5k-P(CDC3.8k-GA7.6k) | | √ | | 89 | 0.14 |

Figure 4:
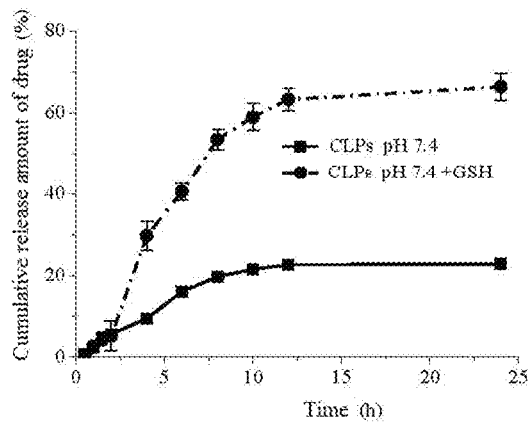
FIG. 4 shows the profile of in vitro release of the DOX.HCl-loaded cross-linked polymeric vesicle PEG5k-P(CDC4.9k-co-TMC19k) prepared by the method of Example 15.

Example 22 Drug Loading and In Vitro Release of the Self-Crosslinked Polymeric Vesicle PEG5k-P(CDC4.9k-co-TMC19k The polymeric vesicles were prepared by solvent displacement method. DOX.HCl was loaded using pH gradient method. The hydrophilic drug DOX.HCl was encapsulated based on the difference between the pH inside and outside the polymeric vesicles. 100 μL of PEG5k-P(CDC4.9k-co-TMC19k) in DMF (10 mg/mL) was added dropwise into 900 μL of sodium citrate/citric acid buffer solution (10 mM, pH 4.0); the solution was placed in a shaker at 37° C. (200 rmp) for 5 hours, then 0.05 mL of PB (4 M, pH 8.1) was added to establish a pH gradient. DOX.HCl was added immediately afterwards. The solution was placed in the shaker for 5 to 10 hours to allow the drug to enter the polymeric vesicles while being self-crosslinked. Finally, the solution was charged into a dialysis bag (MWCO 7000) to be dialyzed overnight, with water being renewed for five times. The dialyzing medium was PB (10 mM, pH 7.4). The self-crosslinked polymeric vesicles loaded with drug in different proportions (10%-30%) had a particle size of 105-124 nm and a particle size distribution of 0.10-0.15. The encapsulation efficiency of DOX.HCl determined by a fluorescence spectrometer was 63%-77%. The in vitro release experiment of DOX.HCl was performed by shaking in a thermostatic shaker at 37° C. (200 rpm), with three replicates in each group. In the first group, the DOX.HCl-loaded self-crosslinked polymeric vesicles were in PB (10 mM, pH 7.4) in which 10 mM GSH was added to simulate the reducing environment in cells; in the second group, the DOX.HCl-loaded self-crosslinked polymeric vesicles were in PB (10 mM, pH 7.4); the concentration of the drug-loaded self-crosslinked polymeric vesicles was 30 mg/L. 0.6 mL was taken therefrom and placed in a dialysis bag (MWCO: 12,000). 25 mL of the corresponding dialysis solvents was added into each test tube. At a predetermined time interval, 5.0 mL of the medium outside the dialysis bag was taken for testing, with 5.0 mL of the corresponding medium being added into the test tube as supplement at the same time. A fluorometer was used to determine the drug concentration in the solution. FIG. 4 was the relationship between the cumulative release amount of DOX.HCl and time. As could be seen in the figure, upon addition of GSH which simulated the reducing environment in tumor cells, the release was significantly faster than that of the samples without adding GSH, suggesting that in the presence of 10 mM of GSH, the drug-loaded self-crosslinked polymeric vesicles could release the drug efficiently.

Example 23 Hydrophobic Drug PTX Loading and Release of the Targeted Self-Crosslinked Polymeric Vesicle Ally-PEG6k-P(CDC2.9k-CL14.2k The polymeric vesicles were prepared by solvent displacement method. 10 μL of paclitaxel PTX in DMF (10 mg/mL) and 90 μL of Ally-PEG6k-P(CDC2.9k-CL14.2k) in DMF (10 mg/mL) were mixed. The mixture was dripped into 900 μL of phosphate buffer solution (10 mM, pH 7.4, PB), placed in a shaker at 37° C. (200 rmp) overnight to be self-crosslinked, and then charged into a dialysis bag (MWCO 7000) overnight for dialysis, with water being renewed for five times, the dialysis medium was PB (10 mM, pH 7.4). The content of PTX was 0-20 wt. %. The self-crosslinked polymeric vesicles obtained had a size of 130-170 nm and a particle size distribution of 0.1-0.2. The structure of polymeric vesicles was measured by TEM and the polymeric vesicles had the reduction-sensitive decrosslinking property. The encapsulation efficiency of PTX was 50%-70%. The in vitro release experiment was designed in the same way as in Example 22, after GSH was added, the release of the hydrophobic drug became significantly faster than the samples without adding GSH.

Figure 5:
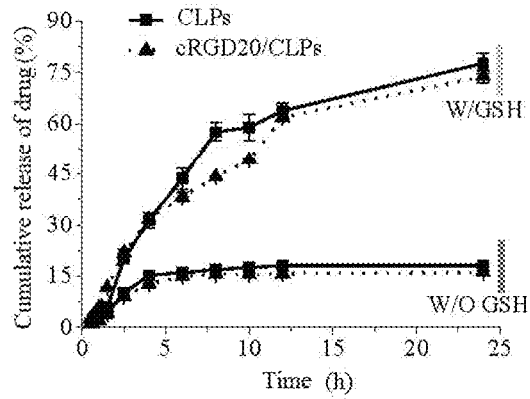
FIG. 5 shows the profile of in vitro release of the DOX.HCl-loaded cross-linked polymeric vesicle cRGD20/PEG6k-P(CDC4.6k-co-TMC18.6k) prepared by the method of Example 24.

Example 24 Drug Loading and Release of the Targeted Self-Crosslinked Polymeric Vesicle cRGD20/PEG6.5k-P(CDC4.6k-co-TMC18.6k The polymeric vesicles were prepared by thin-film hydration method. DOX.HCl was loaded by pH gradient method. 1.6 mg of PEG5k-P(CDC4.9k-co-TMC19k) and 0.4 mg of cRGD-PEG6.5k-P(CDC4.6k-co-TMC18.6k) were dissolved in 0.5 mL of a low-boiling organic solvent, such as methylene chloride or acetonitrile. In a 25-mL flask with pointed bottom, a thin film was formed at the bottom by rotary evaporation, then suction was continued for 24 hours under a vacuum degree of 0.1 mBar. 2 mL of sodium citrate/citric acid buffer solution (10 mM, pH 4.0) was added thereto. The thin film was peeled from the surface by stirring at 37° C., grinded, and then subjected to sonication for 20 min (200 rpm) and continued to stir for 24 hours, so as to be self-crosslinked. According to the measurement by DLS, the cross-linked polymeric vesicles had a size of about 90 nm and a particle size distribution of 0.10. 0.05 mL of PB (4M, pH 8.1) was added to the above solution of polymeric vesicles to establish a pH gradient, followed by adding DOX.HCl immediately. The solution was placed in a shaker for 5-10 hours. It was then charged into a dialysis bag (MWCO 7000) to dialyze against PB overnight, with fluid being renewed for five times. After being loaded with drug at different ratios (10%-30%), the particle size was 112-121 nm, the particle size distribution was 0.10-0.15, and the encapsulation efficiency of DOX.HCl was 61%-77%. The in vitro release experiment was designed in the same way as in Example 22. As could be seen in FIG. 5, after 10 mM of GSH was added, the drug was released efficiently at a speed significantly faster than that of the samples without adding GSH.

Example 25 Drug Loading and Release of the Targeted Self-Crosslinked Polymeric Vesicle cNGQ20/PEG6.5k-P(CDC4.6k-co-TMC18.6k The polymeric vesicles were prepared by dialysis method. Epinibicin hydrochloride (Epi.HCl) was loaded by pH gradient method. 80 μL of PEG5k-P(CDC4.9k-co-TMC19k) in DMF (10 mg/mL) and 20 μL of cNGQ-PEG6.5k-P(CDC4.6k-co-TMC18.6k) in DMF (10 mg/mL) were mixed uniformly and directly charged into a dialysis bag (MWCO 7000) afterwards. In a sodium citrate/citric acid buffer solution (10 mM, pH 4.0), the solution was placed in a shaker at 37° C. for 4 hours to be self-crosslinked, followed by being dialyzed against the same medium for 12 hours, with fluid being renewed for five times. According to the measurement by DLS, the self-crosslinked polymeric vesicles had a size of 96 nm and a particle size distribution of 0.18. 0.05 mL of PB (4M, pH 8.5) was added to the above solution of polymeric vesicles to establish a pH gradient, followed by adding Epi.HCl immediately. The solution was placed in a shaker for 5-10 hours and then charged into a dialysis bag (MWCO 7000) to dialyze against PB overnight, with fluid being renewed for five times. After being loaded with drug at different ratios (10%-30%), the polymeric vesicles had a particle size of 98-118 nm and a particle size distribution of 0.10-0.15, and the encapsulation efficiency of Epi.HCl was 64%-79%. The in vitro release experiment of Epi-HCl was designed in the same way as in Example 22.

Using preparation methods similar to the methods as described above, the drug loading content and encapsulation efficiency of a variety of self-crosslinked polymeric vesicles and targeted self-crosslinked polymeric vesicles could be studied for a variety of hydrophilic anticancer small molecule drugs such as doxorubicin hydrochloride (DOX.HCl), epirubicin hydrochloride (Epi.HCl), irinotecan hydrochloride (CPT.HCl) and mitoxantrone hydrochloride (MTO.HCl), as well as hydrophobic anticancer drugs such as paclitaxel and docetaxel, as could be seen in Table 3.

TABLE 3

Drug Loading content and Encapsulation Efficiency of the Self-Crosslinked Polymeric vesicles and the Targeted Self-Crosslinked Polymeric vesicles for Hydrophilic Drugs

| Polymer/Drug | Feed ratio (wt. %) | Drug loading content (wt. %) | Encapsulation Efficiency (%) | size (nm) | Partical size distribution |
|---|---|---|---|---|---|
| PEG5k-P(CDC3.7k-co-LA14.6k)/DOX•HCl | 0 | — | — | 123 | 0.05 |
|  | 10 | 6.5 | 69.7 | 134 | 0.14 |
|  | 20 | 12.3 | 69.9 | 142 | 0.18 |
|  | 30 | 20.9 | 88.3 | 153 | 0.18 |
| PEG5k-P(CDC4.9k-co-TMC19k)/DOX•HCl | 0 | — | — | 102 | 0.11 |
|  | 10 | 7.1 | 76.5 | 105 | 0.11 |
|  | 20 | 11.9 | 67.6 | 108 | 0.12 |
|  | 30 | 15.9 | 62.9 | 124 | 0.15 |
| cRGD20/PEG5k-P(CDC4.9k-co-TMC19k)/DOX•HCl | 0 | — | — | 88 | 0.08 |
|  | 10 | 7.2 | 77.2 | 112 | 0.10 |
|  | 20 | 11.8 | 66.8 | 116 | 0.13 |
|  | 30 | 15.4 | 60.5 | 121 | 0.15 |
| cNGQ20/PEG5k-P(CDC4.9k-co-TMC19k)/DOX•HCl | 0 | — | — | 96 | 0.18 |
|  | 10 | 7.3 | 79.1 | 98 | 0.10 |
|  | 15 | 10.3 | 76.8 | 105 | 0.13 |
|  | 20 | 11.4 | 64.3 | 118 | 0.15 |
| CC9-PEG6.5k-P(CDC3.8k-co-LA13.8k)/DOX•HCl | 0 | — | — | 134 | 0.09 |
|  | 20 | 13.9 | 80.5 | 168 | 0.21 |
| PEG2k-P(CDC1.9k-TMC4.1k)/DOX•HCl | 0 | — | — | 40 | 0.12 |
|  | 20 | 11.9 | 67.3 | 52 | 0.18 |
| PEG6.5k-P(CDC5.8k-LA28.3k)/Epi•HCl | 0 | — | — | 165 | 0.22 |
|  | 20 | 12.6 | 72.3 | 175 | 0.12 |
| PEG3.4k-P(CDC1.9k-TMC4.1k)/DOX•HCl | 0 | — | — | 57 | 0.19 |
|  | 20 | 11.5 | 64.8 | 63 | 0.17 |
| P(CDC3.8k-TMC18.8k)-PEG5k-P(CDC3.8k-TMC18.8k)/Epi•HCl | 0 | — | — | 143 | 0.21 |
|  | 20 | 12.6 | 71.8 | 172 | 0.26 |
| cRGD20/PEG5k-P(CDC4.9k-co-TMC19k)/CPT•HCl | 20 | 12.6 | 72.1 | 138 | 0.18 |
| cNGQ20/PEG5k-P(CDC4.9k-co-TMC19k)/MTO•HCl | 20 | 6.7 | 35.8 | 108 | 0.10 |
| CC9-P(CDC3.8k-LA18.8k)-PEG4k-P(CDC3.8k-LA18.8k)/CPT•HCl | 20 | 11.9 | 67.5 | 121 | 0.06 |
| Ally-PEG6k-P(CDC2.9k-CL14.2k)/PTX | 20 | 13.5 | 78.1 | 135 | 0.17 |
| $N_3$-PEG1.9k-P(CDC2.7k-PDSC2.6k)/PTX | 20 | 11.4 | 64.3 | 169 | 0.21 |
| AA-PEG3k-P(CDC3.9k-PDSC4.8k)/DTX | 20 | 8.9 | 48.9 | 87 | 0.13 |

Figure 6:
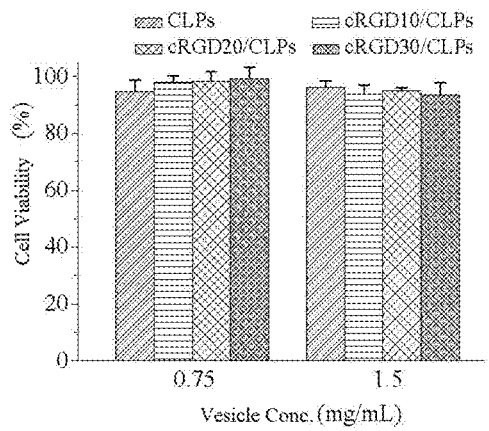
FIG. 6 is a graph showing the toxicity of the targeted cross-linked polymeric vesicle cRGD/PEG6k-P(CDC4.6k-co-TMC18.6k) on A549 lung cancer cells tested by the method of Example 26.

Example 26 Measurement of the Toxicity of the Empty Self-Crosslinked Polymeric Vesicles and the Empty Targeted Self-Crosslinked Polymeric Vesicles on A549 Cells by MTT Assay The cytotoxicity of the empty polymeric vesicles was tested by MTT assay using A549 human lung cancer cells. A549 cells were seeded in a 96-well plate at a density of $5 \times 10^4$ cells/mL, with 100 μL in each well. After 24 hours, the cells were cultured till cell confluency of 70%. Then, the polymeric vesicle samples having different concentrations (0.0001-1.5 mg/mL) were added respectively to each well of the experimental groups (with the empty self-crosslinked polymeric vesicles prepared by the method of Example 15 and the empty targeted self-crosslinked polymeric vesicle cRGD/PEG6.5k-P(CDC4.6k-co-TMC18.6k) of Example 19 as examples). Cell-free control wells and culture medium-free wells (provided in quadruplicate) were additionally provided. After 24 hours of incubation, 10 μL of MTT (5.0 mg/mL) was added to each well. After another 4 hours of incubation, 150 μL of DMSO was added into each well to dissolve the crystals generated. The absorbance (A) at 492 nm was measured by a microplate reader. A zero adjustment was performed with the culture medium-free wells to calculate the cell survival rate. FIG. 6 was the result of the cytotoxicity of the self-crosslinked polymeric vesicles. It could be seen that when the concentration of the cross-linked polymeric vesicles increased from 0.75 to 1.5 mg/mL, the survival rate of A549 was still higher than 90%, indicating that the cross-linked polymeric vesicles had good biocompatibility.

Figure 7:
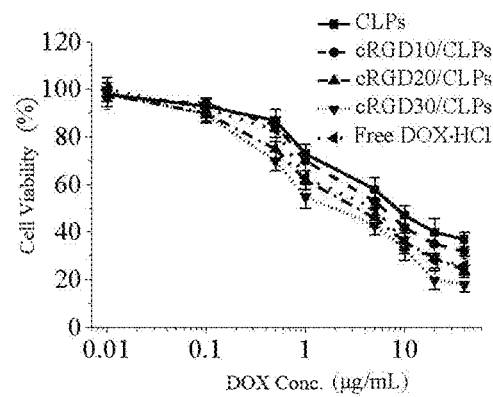
FIG. 7 is a graph showing the toxicity of the DOX.HCl-loaded targeted cross-linked polymeric vesicle cRGD/PEG6k-P(CDC4.6k-co-TMC18.6k) on A549 lung cancer cells tested by the method of Example 26.

Example 27 Measurement of the Toxicity of the Drug-Loaded Self-Crosslinked Polymeric Vesicles and the Drug-Loaded Targeted Self-Crosslinked Polymeric Vesicles on A549 Lung Cancer Cells by MTT Assay The toxicity of the polymeric vesicles on A549 cells was tested by MTT assay. The cells were cultured in the same manner as in Example 26, except that when loading samples in each well of the experimental groups, the drug-loaded cross-linked polymeric vesicles and the drug-loaded targeted self-crosslinked polymeric vesicles, the DOX.HCl-loaded self-crosslinked polymeric vesicles of Example 22, the DOX.HCl-loaded targeted self-crosslinked polymeric vesicles cRGD/PEG6.5k-P(CDC4.6k-co-TMC18.6k) of Example 24 and the DOX.HCl-loaded targeted self-crosslinked polymeric vesicle cNGQ/PEG6.5k-P(CDC4.6k-co-TMC18.6k) of Example 25 were added to each of the corresponding wells. The concentrations of DOX.HCl were 0.01, 0.1, 0.5, 1, 5, 10, 20 and 40 μg/mL, respectively. The content of the targeting molecules ranged from 10%, 20% to 30%; the non-targeted drug-loaded self-crosslinked polymeric vesicle group and the free DOX.HCl group were used as control groups. After co-cultivation for 4 hours, the samples were aspirated and replaced with fresh medium to continue incubation for 44 hours. The subsequent addition of MTT, treatment, and measurement of absorbance were the same as those in Example 26. FIG. 7 was the toxicity of the drug-loaded self-crosslinked polymeric vesicle cRGD/PEG6.5k-P(CDC4.6k-co-TMC18.6k) on A549 cells. It could be seen that the half inhibition concentration ($IC_{50}$) of the DOX.HCl-loaded targeted self-crosslinked polymeric vesicles containing 30% cRGD for A549 cells was 2.13 μg/mL, which was much lower than that of the non-targeted control polymeric vesicles and was also lower than that of free drug (4.89 μg/mL), indicating that the drug-loaded targeted self-crosslinked polymeric vesicles of the present disclosure could target to lung cancer cells efficiently, release drug inside the cells, and eventually kill the cancer cells.

Example 28 Measurement of the Toxicity of the Drug-Loaded Self-Crosslinked Polymeric Vesicles and the Drug-Loaded Targeted Self-Crosslinked Polymeric Vesicles on H460 Cells by MTT Assay MTT assay was used to test the toxicity of the polymeric vesicles on H460 human lung cancer cells. The culture of cells was the same as that in Example 26, except that when the samples were added to each well of the experimental groups, taking the CPT.HCl-loaded targeted self-crosslinked polymeric vesicle CC9/P(CDC3.8k-LA18.8k)-PEG4k-P(CDC3.8k-LA18.8k) as an example, the drug-loaded targeted crosslinked polymeric vesicles containing different cc-9 contents and different drug amounts were added to each corresponding well, the concentrations of CPT.HCl were 0.01, 0.1, 0.5, 1, 5, 10, 20, and 40 g/mL; the content of the targeting molecule ranged from 10%, 20% to 30%; the non-targeted drug-loaded crosslinked polymeric vesicle group and the free CPT.HCl group were used as control groups. After co-cultivation for 4 hours, the samples were aspirated and replaced with fresh medium to continue incubation for 44 hours. The subsequent addition of MTT, treatment, and measurement of absorbance were the same as those in Example 26. The results showed that the $IC_{50}$ of the non-targeted drug-loaded self-crosslinked polymeric vesicles was 4.85 μg/mL for H460 cells; in particular, the $IC_{50}$ of the DOX.HCl-loaded targeted cross-linked polymeric vesicles containing 30% CC9 for H460 cells was 2.17 μg/mL, which was much lower than that of DOX liposomal injection (Libod, DOX-LPs) (35.2 μg/mL), and lower than that of free drug (3.09 μg/mL), indicating that the drug-loaded targeted cross-linked polymeric vesicles of the present disclosure could target to lung cancer cells efficiently, release drug inside the cells, and eventually kill the cancer cells.

The toxicity of a variety of self-crosslinked polymeric vesicles and targeted self-crosslinked polymeric vesicles loaded with drugs on lung cancer cells was studied by methods similar as the method described above. The drug was hydrophilic anticancer small molecule drug such as doxorubicin hydrochloride (DOX.HCl), epirubicin hydrochloride (Epi.HCl), irinotecan hydrochloride (CPT.HCl) and mitoxantrone hydrochloride (MTO.HCl), and hydrophobic anticancer drug such as paclitaxel and docetaxel. The results were shown in Table 4.

Figure 8:
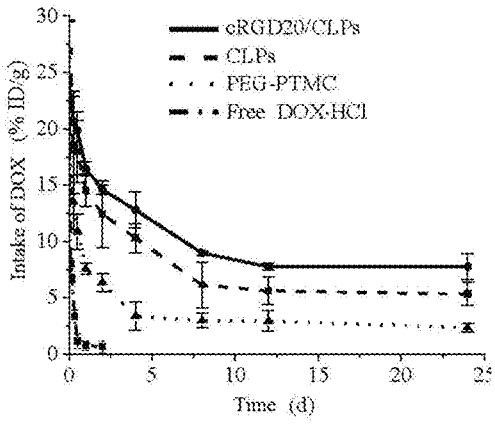
FIG. 8 is a graph showing the study results of the in vivo blood circulation in mice of the DOX.HCl-loaded targeted cross-linked polymeric vesicle cRGD/PEG6k-P(CDC4.6k-co-TMC18.6k) tested by the method of Example 28.

Example 29 Blood Circulation of the Drug-Loaded Self-Crosslinked Polymeric Vesicle CLPs and the Drug-Loaded Targeted Self-Crosslinked Polymeric Vesicle cRGD20/CLPs All operation of the animal experiments conformed to the requirements of the Animal Experimental Center of Soochow University. Balb/C nude mice weighing approximately 18 to 20 grams (aged 4 to 6 weeks) were selected for the experiments. The polymeric vesicles were composed of PEG5k-P(CDC4.9k-co-TMC19k) and a mixture of cRGD-PEG6.5k-P(CDC4.6k-co-TMC18.6k) and PEG5k-P(CDC4.9k-co-TMC19k) mixed at different ratios. When the proportion of cRGD was 20%, the particle size was 100 nm, the particle size distribution was 0.10, the polymeric vesicles were named as cRGD20/CLPs, and the drug was DOX.HCl. The DOX.HCl-loaded non-targeted polymeric vesicle CLPs, the targeted polymeric vesicle cRGD20/CLPs, and the non-crosslinked targeted polymeric vesicle cRGD20/PEG-PTMC and DOX.HCl were injected intravenously via tail vein into the mice (the dose of DOX was 10 mg/kg); about 10 μL of blood was taken at each time point of 0, 0.25, 0.5, 1, 2, 4, 8, 12 and 24 hours. The weight of blood was accurately calculated by a method of weighing by difference; 100 μL of Triton at the concentration of 1% and 500 μL of DMF (containing 20 mM of DTT and 1 M of HCl) were added thereto for extraction; after centrifugation (20,000 rpm, 20 minutes), the supernatant was taken and the amount of DOX.HCl at each time point was measured by fluorescence. In FIG. 8, the abscissa indicated time, and the ordinate indicated the ratio of DOX-HCl per gram blood against the total amount of the injected DOX (ID %/g). As could be seen in the figure, the circulation time of DOX.HCl was very short; DOX could be hardly detected at the time point of 2 hours while there was still 8 ID %/g of the cross-linked polymeric vesicles after 24 hours. By calculation, the elimination half-lives of the targeted drug-loaded self-crosslinked polymeric vesicles, the drug-loaded self-crosslinked polymeric vesicles and the non-crosslinked targeted polymeric vesicles in mice were 4.49, 4.26, and 1.45 hours, respectively, whereas the elimination half-life of DOX-HCl was only 0.27 hours. Therefore, the targeted drug-loaded self-crosslinked polymeric vesicles were stable in mice and had long circulation time. The operation and calculation method of the blood circulation experiments for other drug-loaded targeted self-crosslinked polymeric vesicles and drug-loaded self-crosslinked polymeric vesicles were the same. The results were shown in Table 4.

Figure 9:
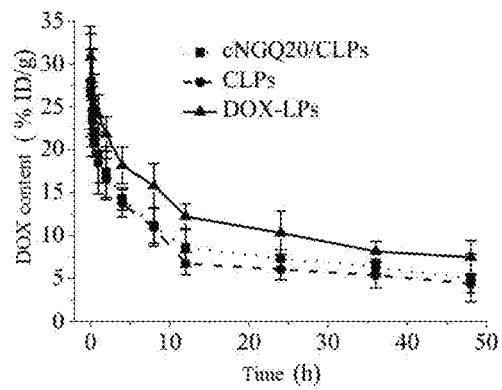
FIG. 9 is a graph showing the study results of the in vivo blood circulation in mice of the DOX.HCl-loaded targeted cross-linked polymeric vesicle cNGQ/PEG6k-P(CDC4.6k-co-TMC18.6k) tested by the method of Example 29.

Example 30 Blood Circulation of the Drug-Loaded Self-Crosslinked Polymeric Vesicle CLPs and the Drug-Loaded Targeted Self-Crosslinked Polymeric Vesicle cNGQ20/CLPs As Example 25, after being loaded with DOX.HCl, the targeted self-crosslinked polymeric vesicle cNGQ20/CLPs consisting of cNGQ-PEG6.5k-P(CDC4.6k-co-TMC18.6k) and PEG5k-P(CDC4.9k-co-TMC19k), and the non-targeted self-crosslinked polymeric vesicle CLPs were injected intravenously via tail vein into the Balb/C nude mice. The blood circulation was studied in the same manner as in Example 29. DOX.HCl and liposomal adriamycin (Libod DOX-LPs) were used in the control groups. The results were as shown in FIG. 9, there still remained 5.0 ID %/g of cNGQ20/CLPs and CLPs after 48 hours. By calculation, the elimination half-lives of the targeted self-crosslinked polymeric vesicles and the self-crosslinked polymeric vesicles in mice were 4.99 and 4.79 hours, respectively. Therefore, they were stable in mice and had long circulation time. The results were shown in Table 4.

Example 31 In Vivo Imaging of the Self-Crosslinked Polymeric Vesicles and the Targeted Self-Crosslinked Polymeric Vesicles in Mice Bearing A549 Lung Cancer Balb/C nude mice weighing approximately 18 to 20 grams (aged 4 to 6 weeks) were selected for the in vivo imaging experiment. $5 \times 10^6$ A549 human lung cancer cells were injected subcutaneously. After about 3 to 4 weeks, the experiment was started when the tumor size reached 100 to 200 mm³. The self-crosslinked polymeric vesicle cRGD20/CLPs prepared from cRGD-PEG6.5k-P(CDC4.6k-co-TMC18.6k) and PEG5k-P(CDC4.9k-co-TMC19k), and the non-targeted self-crosslinked polymeric vesicle CLPs were taken as example. cRGD20/CLPs and the non-targeted CLPs labeled by a fluorescent substance cy-7 were injected intravenously via tail vein into the mice, and the whereabouts of the polymeric vesicles were tracked with in vivo imaging system for small animals at different time points of 1, 2, 4, 6, 8, 12, 24, and 48 hours. According to the experimental results, cRGD20/CLPs accumulated rapidly at the tumor site and the fluorescence remained strong after 48 hours, indicating that cRGD20/CLPs had the ability of active targeting and could be enriched to the tumor site. The operation and calculation method of the in vivo imaging experiments for other targeted self-crosslinked polymeric vesicles and self-crosslinked polymeric vesicles were the same. The results were shown in Table 4.

Example 32 In Vivo Imaging Experiment of the Drug-Loaded Self-Crosslinked Polymeric Vesicle CLPs and the Drug-Loaded Targeted Self-Crosslinked Polymeric Vesicle cNGQ20/CLPs in Mice Bearing A549 Lung Cancer Tumor inoculation and administration via tail vein in the in vivo imaging experiment were the same as those in Example 31. CLPs and cNGQ20/CLPs which were loaded with Epi.HCl and labeled by cy-7 were prepared as described in Example 25, and were both found to rapidly accumulate at the tumor site. CLPs disappeared within 4-6 hours while the fluorescence of cNGQ20/CLPs at the tumor site was still strong after 48 hours, which meant that cNGQ20/CLPs had the ability of active targeting and could be enriched to the tumor site. The results were in Table 4.

Example 33 In Vivo Imaging Experiment of the Drug-Loaded Self-Crosslinked Polymeric Vesicle CLPs and the Drug-Loaded Targeted Self-Crosslinked Polymeric Vesicle CC9/CLPs in Mice Bearing H460 Lung Cancer Balb/C nude mice weighing approximately 18 to 20 grams (aged 4 to 6 weeks) were selected for the in vivo imaging experiment. $5 \times 10^6$ H460 lung cancer cells were injected subcutaneously. After about 3 to 4 weeks, the experiment was started when the tumor size reached 100 to 200 mm$^3$. The targeted self-crosslinked polymeric vesicle CC9/CLPs prepared from CC9-PEG6.5k-P(CDC3.8k-co-LA13.8k) and PEG5k-P(CDC3.7k-co-LA14.6k), and the drug-loaded self-crosslinked polymeric vesicle CLPs were labeled with cy-5 and loaded with the hydrophobic drug docetaxel DTX. The in vivo imaging was studied by the same operation as that in Example 32. According to experimental results, DTX-loaded CC9/CLPs could rapidly accumulate at the tumor site and the fluorescence thereof at the tumor site still remained strong after 48 hours, which meant that CC9/CLPs had the ability of active targeting and could be enriched to the tumor site. In contrast, the drug-loaded non-targeted self-crosslinked polymeric vesicles were soon metabolized within 2 hours after entering the tumor and the fluorescence intensity was low. The results were shown in Table 4.

Figure 10:
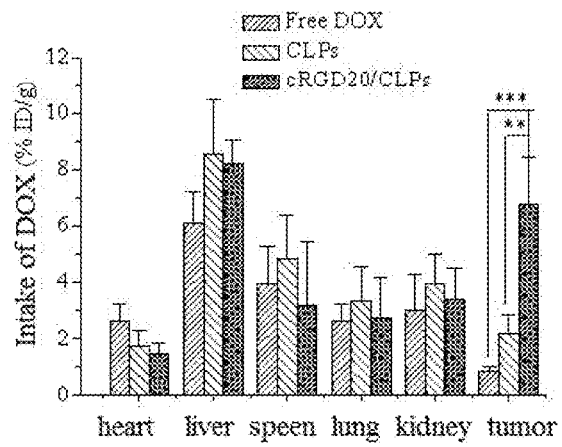
FIG. 10 is a graph showing the biodistribution results of the DOX.HCl-loaded targeted cross-linked polymeric vesicle cRGD/PEG6k-P(CDC4.6k-co-TMC18.6k) in mice bearing subcutaneous lung cancer tested by the method of Example 33.

Example 34 In Vivo Biodistribution of the Drug-Loaded Self-Crosslinked Polymeric Vesicle CLPs and the Drug-Loaded Targeted Self-Crosslinked Polymeric Vesicle cRGD20/CLPs in Mice Bearing A549 Lung Cancer Tumor inoculation and administration via tail vein in the in vivo imaging experiment were the same as those in Example 31. The DOX.HCl-loaded targeted self-crosslinked polymeric vesicle cRGD20/CLPs prepared from cRGD-PEG6.5k-P(CDC4.6k-co-TMC18.6k) and PEG5k-P(CDC4.9k-co-TMC19k), and the non-targeted self-crosslinked polymeric vesicle CLPs were injected intravenously via tail vein into mice (DOX.HCl: 10 mg/kg). After 12 hours, the mice were sacrificed, and the tumor and the tissues including heart, liver, spleen, lung and kidney were taken out. After being washed and weighed, 500 µL of 1% Triton was added and the above tissues were grinded by a homogenizer, and then 900 µL of DMF (containing 20 mM DTT, 1 M HCl) was added thereto for extraction. After centrifugation (20,000 rpm, 20 minutes), the supernatant was taken to measure the amount of DOX.HCl at each time point by fluorescence. In FIG. 10, the abscissa indicated the tissues and organs, the ordinate indicated the ratio of DOX.HCl per grain tumor or tissue against the total amount of the injected DOX.HCl (D %/g). The amount of DOX.HCl accumulated in the tumors at the time point of 12 hours after the injection of cRGD20/CLPs, CLPs and DOX.HCl was 6.54, 2.53, and 1.02 ID %/g, respectively, the amount of the accumulated DOX.HCl of cRGD20/CLPs was 3 and 6 times that of CLPs and DOX.HCl, which indicated that the drug-loaded cRGD20/CLPs accumulated more at the tumor site through active targeting. The results were shown in Table 4.

Figure 11:
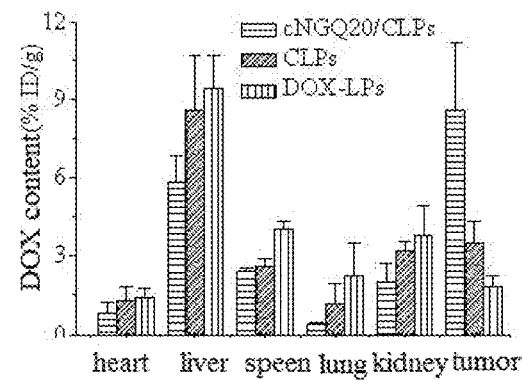
FIG. 11 is a graph showing the biodistribution results of the DOX.HCl-loaded targeted cross-linked polymeric vesicle cNGQ/PEG6k-P(CDC4.6k-co-TMC18.6k) in mice bearing subcutaneous lung cancer tested by the method of Example 34.

Example 35 In Vivo Biodistribution of the Drug-Loaded Self-Crosslinked Polymeric Vesicle CLPs and the Drug-Loaded Targeted Self-Crosslinked Polymeric Vesicle cNGQ/CLPs in Mice Bearing A549 Lung Cancer The tumor inoculation, administration via tail vein and the operations of animals were the same as those in Example 34. The DOX.HCl-loaded cNGQ20/CLPs, the non-targeted CLPs, and liposomal adriamycin (Libod DOX-LPs) were injected intravenously via tail vein into mice (DOX.HCl: 10 mg/kg). After 6 hours, the amount of DOX.HCl accumulated at the tumor site of cNGQ20/CLPs, CLPs, and DOX-LP was 8.63, 3.52, and 1.82 ID %/g, respectively, the amount of the accumulated DOX.HCl of cNGQ20/CLPs was 2 and 5 times that of the latter two, which meant that the drug-loaded cNGQ20/CLPs accumulated more at the tumor site through active targeting. The results were shown in FIG. 11.

Example 36 In Vivo Biodistribution of the Drug-Loaded Self-Crosslinked Polymeric Vesicle CLPs and the Drug-Loaded Targeted Self-Crosslinked Polymeric Vesicle CC9/CLPs in Mice Bearing H460 Lung Cancer The establishment of an H460 lung cancer-bearing mice model was performed in the same manner as in Example 33. The administration via tail vein and the operations of animals were the same as those in Example 34. The DTX-loaded CC9/CLPs, the non-targeted CLPs, and DOX-LPs were administered intravenously via tail vein. After 6 hours, the amount of DTX accumulated in the tumor of CC9/CLPs, CLPs, and DOX-LPs was 9.02, 2.42, and 1.82 ID %/g, respectively, the amount of the accumulated DTX of CC9/CLPs was 4 and 5 times that of CLPs and DOX-LPs, which meant that the drug-loaded CC9/CLPs accumulated at the tumor site through active self-targeting, as shown in Table 4.

Figure 12:
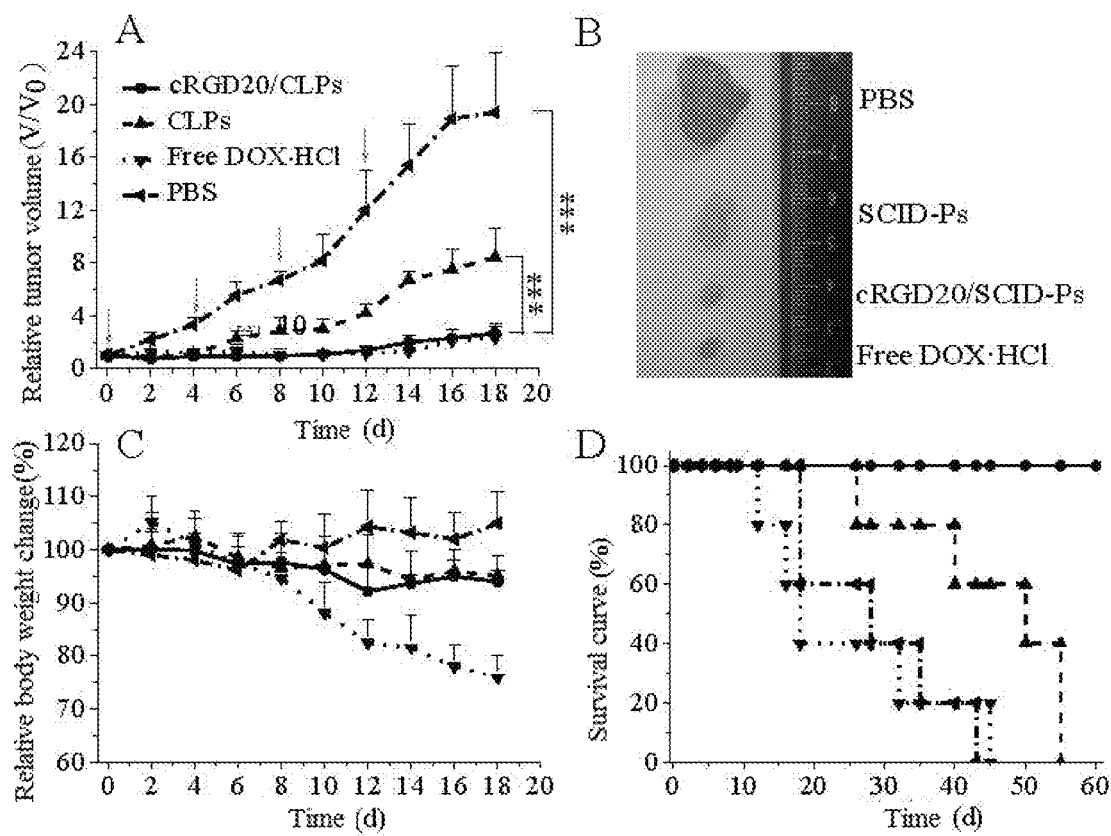
FIG. 12 shows the treatment profile of the DOX.HCl-loaded targeted cross-linked polymeric vesicle cRGD/PEG6k-P(CDC4.6k-co-TMC18.6k) in mice bearing subcutaneous lung cancer tested by the method of Example 36, wherein A is the tumor growth curve, B is the picture of tumors after mice being treated, C is the body weight changes, and D is the survival curve.

Example 37 Anti-Tumor Effect of the Drug-Loaded Targeted Self-Crosslinked Polymeric Vesicle cRGD20/CLPs and the Drug-Loaded Self-Crosslinked Polymeric Vesicle CLPs, Body Weight Changes and Survival Rate in Mice Bearing A549 Subcutaneous Lung Cancer Balb/C nude mice weighing approximately 18 to 20 grams (aged 4 to 6 weeks) were selected for the experiment and were subcutaneously injected with $5 \times 10^6$ A549 human lung cancer cells. After about two weeks, the experiment was started when the tumor size reached 30 to 50 mm$^3$. The DOX.HCl-loaded targeted self-crosslinked polymeric vesicle cRGD20/CLPs prepared by mixing cRGD-PEG6.5k-P(CDC4.6k-co-TMC18.6k) and PEG5k-P(CDC4.9k-co-TMC19k) at a ratio of 1:5, CLPs, free DOX.HCl and PBS were injected intravenously via tail vein into the mice on Day 0, 4, 8 and 12, respectively (the dose of DOX was 10 mg/kg). On Day 0 to Day 18, the body weights of the mice were measured every two days. The volumes of the tumor were measured by a vernier caliper. The tumor volume was calculated as: V=(L×W×H)/2 (wherein L was the tumor length, W was the tumor width, and H was the tumor thickness). The survival of the mice were observed up to 45 days. As could be seen in FIG. 12, on Day 18, the tumors were significantly inhibited in the cRGD20/CLPs treatment group, while tumors in the drug-loaded CLPs group had a certain growth. Although DOX.HCl could also inhibit the growth of tumor, the body weights of the mice in the free DOX.HCl group decreased by 21% till Day 12, indicating great toxic and side effects on mice. In contrast, the body weights of the mice in the cRGD20/CLPs group and CLPs groups barely changed, indicating that the drug-loaded self-crosslinked polymeric vesicles had no toxic and side effects on mice. All of the mice in the cRGD20/CLPs treatment group survived after 60 days; those in the DOX-.HCl group all had been dead till Day 42, those in the PBS group all had been dead till Day 43. Therefore, the targeted self-crosslinked polymeric vesicles of the present disclosure could effectively inhibit the growth of tumor after being loaded with drugs, had no toxic and side effects on mice, and could also prolong the survival period of the tumor-bearing mice.

Figure 13:
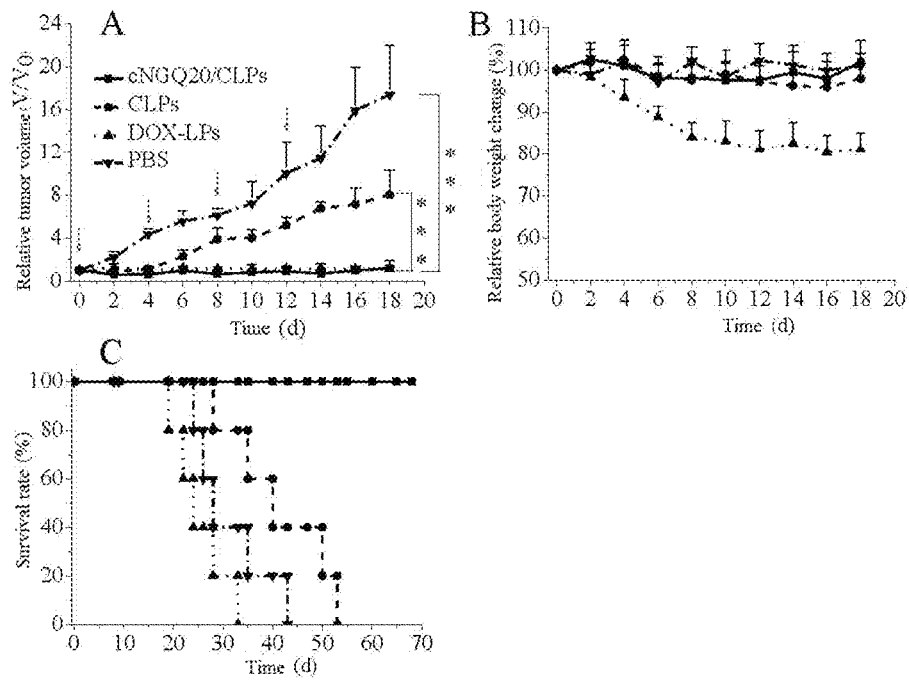
FIG. 13 shows the treatment profile of the DOX.HCl-loaded targeted cross-linked polymeric vesicle cNGQ/PEG6k-P(CDC4.6k-co-TMC18.6k) in mice bearing subcutaneous lung cancer tested by the method of Example 37, wherein A is the tumor growth curve, B is the curve of body weight changes, C is the survival curve.

Example 38 Anti-Tumor Effect of the Drug-Loaded Targeted Self-Crosslinked Polymeric Vesicle cNGQ/CLPs and the Drug-Loaded Self-Crosslinked Polymeric Vesicle CLPs, Body Weight Changes and Survival Rate in Mice Bearing A549 Subcutaneous Lung Cancer The establishment of a subcutaneous A549 tumor-bearing mice model, administration via tail vein, and data collection were the same as those in Example 37. The DOX-HCl-loaded targeted self-crosslinked versicle cNGQ20/CLPs prepared by mixing cNGQ-PEG6.5k-P(CDC4.6k-co-TMC18.6k) and PEG5k-P(CDC4.9k-co-TMC19k) at a ratio of 1:5, the non-targeted CLPs, DOX-LPs, and PBS were injected intravenously via tail vein. As could be seen in FIG. 13, on Day 18, the tumors had been significantly inhibited in the cNGQ20/CLPs treatment group, while the tumors in the drug-loaded CLPs group grew, and the body weights of the mice barely changed. Although DOX-LPs could also inhibit the growth of tumor, the weight of mice in the DOX-LPs group decreased by 18% on Day 12, indicating great toxic and side effect on mice. The mice in the cNGQ20/CLPs treatment group all survived on Day 68, those in the DOX-.HCl group all had been dead till Day 32, and those in the PBS group all had been dead till Day 42. Therefore, the drug-loaded targeted self-crosslinked polymeric vesicles could effectively inhibit tumors with no toxic and side effects on mice, and could prolong the survival period of tumor-bearing mice.

Example 39 Anti-Tumor Effect of the Drug-Loaded Targeted Self-Crosslinked Polymeric Vesicle CC9/CLPs and the Drug-Loaded Self-Crosslinked Polymeric Vesicle CLPs, Body Weight Changes and Survival Rate in Mice Bearing H460 Subcutaneous Lung Cancer The establishment of a subcutaneous H460 tumor-bearing mice model was the same as that in Example 33. The administration via tail vein and data collection were performed in the same manner as in Example 37. The experiment was started when the tumor size reached 30 to 50 mm$^3$. The CPT.HCl-loaded targeted self-crosslinked polymeric vesicle CC9/CLPs prepared by mixing CC9-PEG6.5k-P(CDC3.8k-co-LA13.8k) and PEG5k-P(CDC3.7k-co-LA14.6k) at a ratio of 1:5, the non-targeted CLPs, free CPT.HCl and PBS were injected intravenously via tail vein. The results showed that on Day 18, tumors treated by CC9/CLPs were significantly inhibited, whereas tumor volumes of the drug-loaded CLPs group increased slightly, and the body weights of the mice barely changed. Although CPT.HCl could also inhibit the growth of tumor, the weight of mice in the CPT.HCl group decreased by 18% on Day 10. The mice in the CC9/CLPs treatment group all survived after Day 72, those in the CPT.HCl group all had been dead till Day 28, and those in the PBS group also all had been dead till Day 37.

Figure 14:
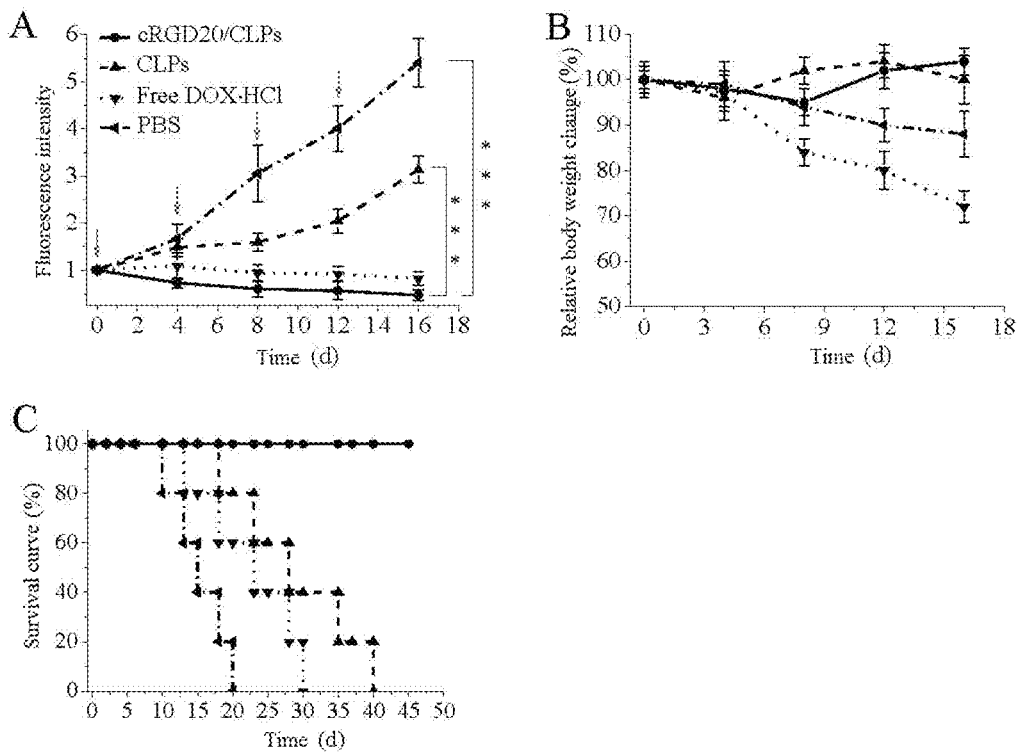
FIG. 14 shows the treatment profile of the DOX.HCl-loaded targeted cross-linked polymeric vesicle cRGD/PEG6k-P(CDC4.6k-co-TMC18.6k) in mice bearing orthotopic lung cancer tested by the method of Example 39, wherein A is the tumor growth curve, B is the curve of body weight changes, C is the survival curve.

Example 40 Anti-Tumor Effect of the Drug-Loaded Targeted Self-Crosslinked Polymeric Vesicle cRGD20/CLPs and the Drug-Loaded Self-Crosslinked Polymeric Vesicle CLPs, Body Weight Changes and Survival Rate in Mice Bearing Orthotopic A549 Lung Cancer Balb/C nude mice weighing approximately 18 to 20 grams (aged 4 to 6 weeks) were selected for the experiment. $5 \times 10^6$ bioluminescent A549 human lung cancer cells (A549-Luc) were directly injected in the lungs. After about 10 days, the mice were observed by an in vivo imaging system for small animals. The lungs of mice showed fluorescence, thus successfully establishing an orthotopic A549 lung cancer model. And then, as in Example 20, the DOX.HCl-loaded targeted self-crosslinked polymeric vesicle cRGD20/CLPs prepared by mixing cRGD-PEG6.5k-P(CDC4.6k-co-TMC18.6k) and PEG5k-P(CDC4.9k-co-TMC19k) at a ratio of 1:5, CLPs, DOX.HCl, and PBS were injected intravenously via tail vein into mice on Days 0, 4, 8 and 12 (DOX.HCl: 10 mg/kg). From Day 0 to Day 16, the body weights of the mice were measured every four days. The bioluminescence intensity of the lung tumor in mice was monitored using an in vivo imaging system for small animals. The survival of the mice was observed up to 45 days. As shown in FIG. 14, the bioluminescence intensity of the lung tumor in the cRGD20/CLPs treatment group continuously decreased within 16 days while the bioluminescence intensity of the lung tumor in the drug-loaded CLPs group increased to some extent. But the body weights of the mice in these two groups barely changed. Although DOX.HCl could also inhibit the growth of tumor, the weights of the mice in the DOX.HCl group decreased by 21% on Day 4, indicating great toxic and side effect on mice. The mice in the cRGD20/CLPs treatment group all survived after 45 days, the mice in the DOX.HCl group had all been dead till Day 30, and the mice in the PBS group also had all been dead till Day 20. Therefore, the drug-loaded targeted self-crosslinked polymeric vesicle cRGD20/CLPs could effectively inhibit the growth of orthotopic lung tumor with no toxic and side effects on mice, and effectively prolong the survival period of the tumor-bearing mice.

Figure 15:
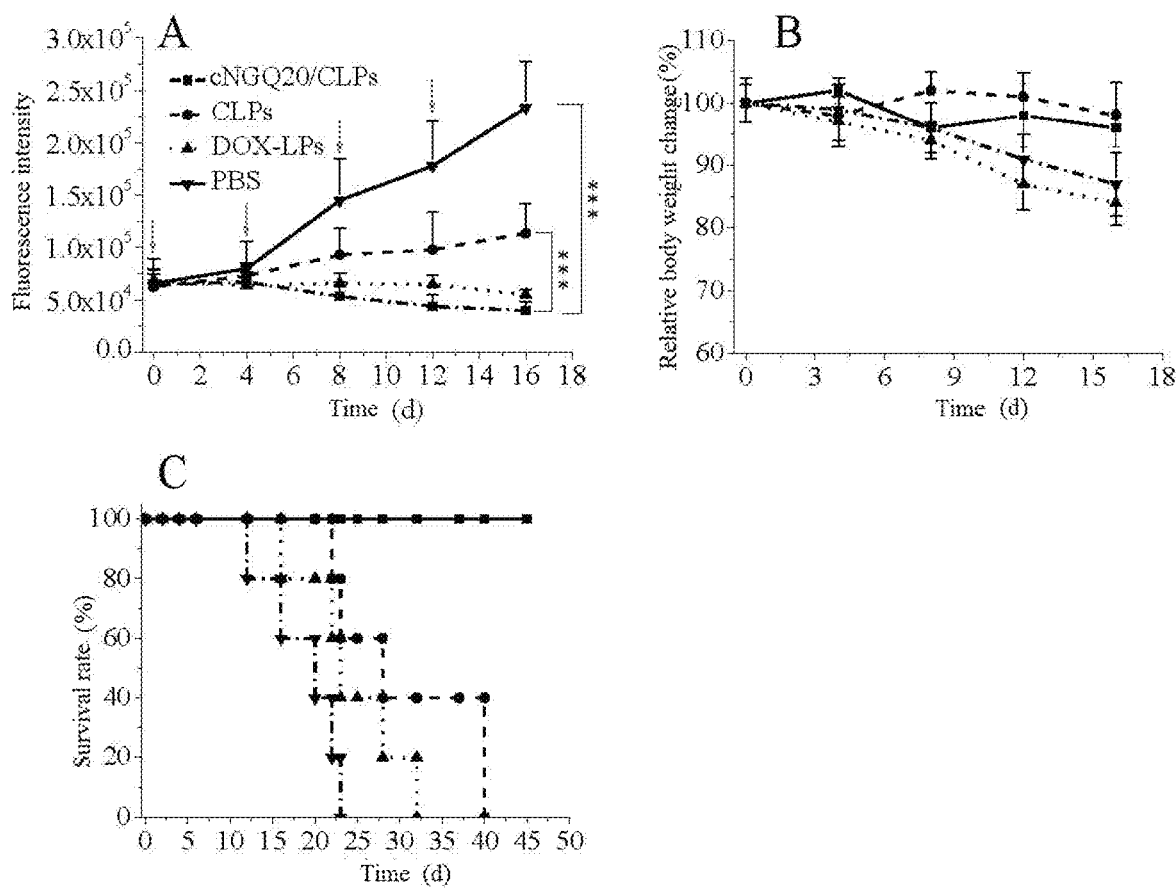
FIG. 15 shows the treatment profile of the DOX.HCl-targeted cross-linked polymeric vesicle cNGQ/PEG6k-P(CDC4.6k-co-TMC18.6k) in mice bearing orthotopic lung cancer tested by the method of Example 40, wherein A is the tumor growth curve, B is the curve of body weight changes, C is the survival curve.

Example 41 Anti-Tumor Effects of the Drug-Loaded Targeted Self-Crosslinked Polymeric Vesicle cNGQ20/CLPs and the Drug-Loaded Self-Crosslinked Polymeric Vesicle CLPs, Body Weight Changes, and Survival Rate in Mice Bearing Orthotopic A549 Lung Cancer The establishment of an orthotopic A549 lung cancer-bearing mice model, mode of administration and detection mode were the same as those in Example 40. The DOX-HCl-loaded targeted self-crosslinked polymeric vesicle cNGQ20/CLPs prepared by mixing cNGQ-PEG6.5k-P(CDC4.6k-co-TMC18.6k) and PEG5k-P(CDC4.9k-co-TMC19k) at a ratio of 1:5, the non-targeted CLPs, DOX- LPs, and PBS were injected intravenously via tail vein. The results were shown in FIG. 15. The bioluminescence intensity of the tumors in the cNGQ20/CLPs treatment group continuously decreased within 16 days, while the bioluminescence intensity of the tumors in the drug-loaded CLP group increased to an extent, and the body weights barely changed. Although DOX-LPs could also inhibit the tumor growth, the body weights of mice in DOX-LPs group decreased by 21% till Day 4. The mice in the cNGQ20/CLPs treatment group all survived after Day 45, the mice in the DOX-LPs group all had been dead till Day 32, and the mice in the PBS group also had all been dead till Day 23. Therefore, the drug-loaded targeted self-crosslinked polymeric vesicle cNGQ20/CLPs could also effectively inhibit the growth of orthotopic lung tumor with no toxic and side effects on mice, and could also prolong the survival period of the tumor-bearing mice.

Example 42 Anti-Tumor Effect of the Drug-Loaded Targeted Self-Crosslinked Polymeric Vesicle CC9/CLPs and the Drug-Loaded Self-Crosslinked Polymeric Vesicle CLPs, Body Weight Changes and Survival Rate in Mice Bearing A549 Orthotopic Lung Cancer The establishment of an orthotopic A549 lung cancer-bearing mice model, mode of administration and detection mode were the same as those in Example 40. The CPT.HCl-loaded targeted self-crosslinked polymeric vesicle CC9/CLP prepared by mixing cc9-PEG6.5k-P(CDC3.8k-co-LA13.8k) and PEG5k-P(CDC3.7k-co-LA14.6k) at a ratio of 1:5, the non-targeted CLPs, CPT.HCl, and PBS were injected into the mice. On Day 16, the bioluminescence intensity of the tumors in the CC9/CLPs treatment group weakened while the bioluminescence intensity of the tumors in the drug-loaded CLPs group increased to an extent, the body weights of the mice barely changed. Although CPT.HCl could also inhibit the growth of tumor, the weights of mice in the CPT.HCl group decreased by 21% till Day 3, indicating great toxic and side effects on mice. The mice in the CC9/CLPs treatment group survived after Day 40, the mice in the CPT.HCl group had all been dead till Day 34, and the mice in the PBS group had all been dead till Day 21. Therefore, the drug-targeted self-crosslinked polymeric vesicle CC9/CLPs could effectively inhibit the growth of orthotopic lung cancer with no toxic and side effects, and could prolong the survival period of the tumor-bearing mice.

Example 43 Anti-Tumor Effect of the Drug-Loaded Cross-Linked Polymeric Vesicle cRGD/CLPs and the Drug-Loaded Self-Crosslinked Polymeric Vesicle CLPs, Body Weight Changes, and Survival Rate in Mice Bearing Orthotopic A549 Lung Cancer The PTX-loaded self-crosslinked polymeric vesicles were prepared by mixing AA-PEG3k-P(CDC3.9k-PDSC4.8k) and PEG1.9k-P(CDC3.6k-PDSC4.6k) at a ratio of 1:5. The PTX-loaded targeted self-crosslinked polymeric vesicle cRGD/CLP were then prepared as in Example 21 by the Michael addition reaction of the acrylate (AA) and the sulfhydryl group of cRGDfC on the surface of the polymeric vesicles. According to the measurement by DLS, the polymeric vesicles had a size of 85 nm and a particle size distribution of 0.10. The grafting ratio of the polypeptide was calculated to be 92% by the analysis of NMR and BCA protein kits.

The establishment of the orthotopic A549 lung cancer-bearing mice model, mode of administration, and detection mode were the same as those in Example 40. The PTG-loaded cRGD/CLPs, the non-targeted self-crosslinked polymeric vesicle CLPs, Taxol, and PBS were injected into mice, respectively. Within 16 days, the bioluminescence intensity of the tumors of the mice in the PTX-loaded cRGD/CLPs treatment group continuously weakened while the bioluminescence intensity of the tumors of the mice in the non-targeted CLPs group increased. The body weights of the mice in these two groups barely changed. Although PTX could also inhibit the growth of tumor, the body weights of mice in the PTX group decreased by 10% till Day 12, indicating great toxic and side effect on mice. The mice in the PTX-loaded cRGD/CLPs treatment group survived on Day 41, the mice in the PTX group all had been dead till Day 29, and the mice in the PBS group all had been dead till Day 32. Therefore, the PTX-loaded cRGD/CLPs could effectively inhibit the growth of orthotopic lung tumor with no toxic and side effects, and could prolong the survival period of the tumor-bearing mice.

The effects of a variety of self-crosslinked polymeric vesicles and targeted self-crosslinked polymeric vesicles loaded with different drugs on mice bearing lung cancer were investigated using experimental methods similar to the methods described above. The results were shown in Table 4.

TABLE 4

In Vivo and In Vitro Anti-tumor Results of the Drug-loaded Self-crosslinked Polymeric vesicles and the Drug-loaded Targeted Self-crosslinked Polymeric vesicle against Lung Cancer

| Polymer/Drug | 24 h/pH 7.4 in vitro release (%) | | Survival rate of lung cancer cell % | | $IC_{50}$ (μg/mL) | Elimination half-life in circulation (h) | Amount of the accumulated drug in tumor (% ID/g) | Survival period of the treated tumor-bearing mice (d) | |
|---|---|---|---|---|---|---|---|---|---|
| | No GSH | 10 mM GSH | Empty vesicle | Drug-loaded vesicle | | | | Subcutaneous model | Orthotopic model |
| PEG5k-P(CDC4.9k-co-TMC19k)/DOX•HCl | 14 | 78 | >90 | 43.5 | 8.92 | 4.79 | 3.52 | 38 | 40 |
| PEG5k-P(CDC3.7k-co-LA14.6k)/DOX•HCl | 17 | 76 | >89 | 37.9 | 9.75 | 4.32 | 2.24 | 36 | 42 |
| cRGD20/PEG5k-P(CDC4.9k-co-TMC19k)/DOX•HCl | 21 | 81 | >90 | 21.6 | 2.13 | 4.49 | 6.54 | >60 | >45 |

TABLE 4-continued

In Vivo and In Vitro Anti-tumor Results of the Drug-loaded Self-crosslinked Polymeric vesicles and the Drug-loaded Targeted Self-crosslinked Polymeric vesicle against Lung Cancer

| Polymer/Drug | 24 h/pH 7.4 in vitro release (%) No GSH | 24 h/pH 7.4 in vitro release (%) 10 mM GSH | Survival rate of lung cancer cell % Empty vesicle | Survival rate of lung cancer cell % Drug-loaded vesicle | IC$_{50}$ (µg/mL) | Elimination half-life in circulation (h) | Amount of the accumulated drug in tumor (% ID/g) | Survival period of the treated tumor-bearing mice (d) Subcutaneous model | Survival period of the treated tumor-bearing mice (d) Orthotopic model |
|---|---|---|---|---|---|---|---|---|---|
| cNGQ20/PEG5k-P(CDC4.9k-co-TMC19k)/DOX•HCl | 23 | 82 | >91 | 16.8 | 1.92 | 4.99 | 8.63 | >68 | >45 |
| PEG1.9k-P(CDC1.9k-TMC4.1k)/Epi•HCl | 19 | 87 | >95 | 41.2 | 9.87 | 3.87 | 1.89 | 28 | 20 |
| CC9/PEG6.5k-P(CDC3.8k-co-LA13.8k)/DTX | 24 | 76 | >88 | 22.7 | 3.06 | 5.04 | 9.02 | >72 | >40 |
| PEG6.5k-P(CDC5.8k-LA28.3k)/CPT•HCl | 21 | 79 | >93 | 35.9 | 7.89 | 4.14 | 2.37 | 32 | 25 |
| Ally-PEG6k-P(CDC2.9k-CL14.2k)/PTX | 20 | 83 | >88 | 22.8 | 8.19 | 4.58 | 3.18 | 38 | 23 |
| N$_3$-PEG1.9k-P(CDC2.7k-PDSC2.6k)/PTX | 16 | 78 | >91 | 41.5 | 7.32 | 4.37 | 2.98 | 41 | 31 |
| AA-PEG3k-P(CDC3.9k-PDSC4.8k)/DTX | 18 | 79 | >90 | 32.6 | 8.17 | 5.15 | 2.73 | 35 | 29 |

What is claimed is:

1. A tumor-specific targeted biodegradable amphiphilic polymer, wherein the tumor-specific targeted biodegradable amphiphilic polymer is prepared by bonding a biodegradable amphiphilic polymer to a targeting molecule and wherein the targeting molecule is cRGD, cNGQ or cc-9;

wherein the chemical structure of the biodegradable amphiphilic polymer is one of the following structures:

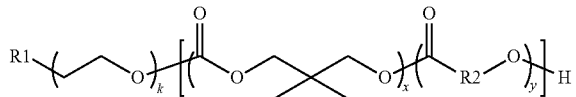

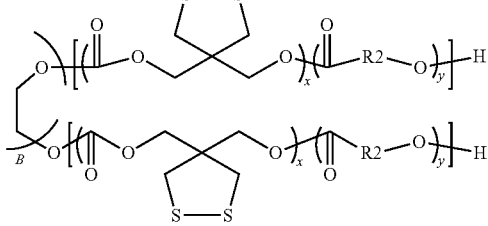

wherein R1 is selected from one of the following groups:

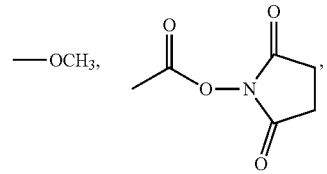

-continued

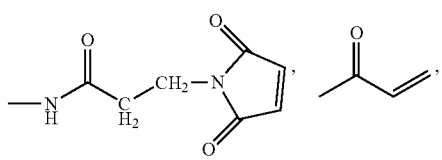

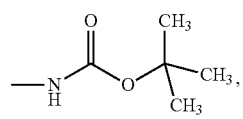

R2 is selected from one of the following groups:

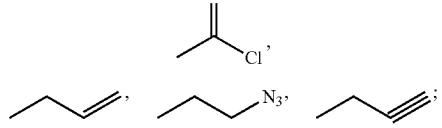

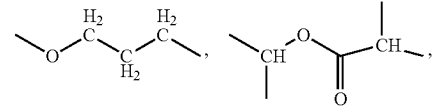

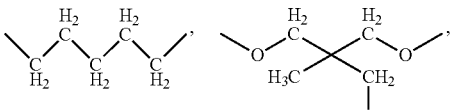

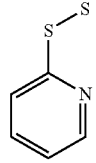

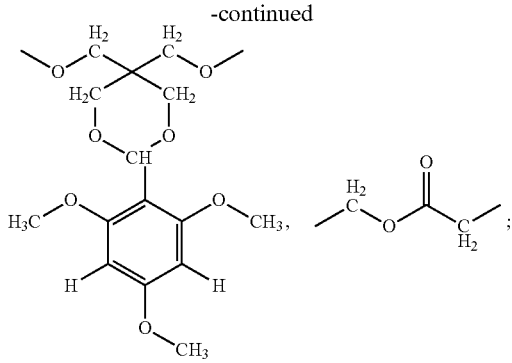

wherein k ranges from 43 to 170, x ranges from 10 to 30, y ranges from 40 to 200, m ranges from 86 to 340.

2. A polymeric vesicle, wherein the polymeric vesicle is prepared by the tumor-specific targeted biodegradable amphiphilic polymer according to claim 1.

3. The polymeric vesicle according to claim 2, wherein the polymeric vesicle is a self-crosslinked polymeric vesicle; and the self-crosslinked polymeric vesicle has a particle size of 40-180 nm.

4. A drug-loaded polymeric vesicle comprising the polymeric vesicle according to claim 2 as a carrier and a drug for lung cancer treatment.

5. The drug-loaded polymeric vesicle according to claim 4, wherein the drug for lung cancer treatment is a hydrophilic anticancer drug or a hydrophobic anticancer drug.

6. A nanomedicine for lung cancer treatment comprising the tumor-specific targeted biodegradable amphiphilic polymer according to claim 1 as a carrier.

7. A nanomedicine for lung cancer treatment comprising the polymeric vesicle according to claim 2 as a carrier.

8. The tumor-specific targeted biodegradable amphiphilic polymer according to claim 1, wherein the tumor is lung cancer.

9. The tumor-specific targeted biodegradable amphiphilic polymer according to claim 1, wherein the R1 is selected from one of the following groups:

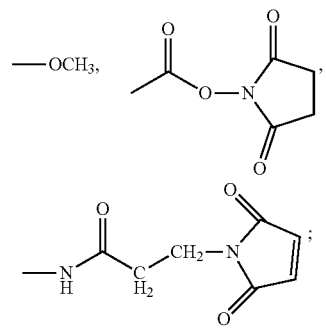

the R2 is selected from one of the following groups:

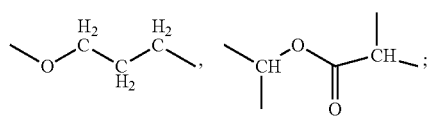

the k ranges from 113 to 170, the x ranges from 20 to 26, the y ranges from 100 to 190, the m ranges from 226 to 340.

* * * * *